(12) United States Patent
Shea et al.

(10) Patent No.: US 7,223,592 B2
(45) Date of Patent: May 29, 2007

(54) DEVICES AND METHODS FOR PERFORMING ARRAY BASED ASSAYS

(75) Inventors: Laurence R. Shea, Charlotte, NC (US); Douglas G. Summers, Sunnyvale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 653 days.

(21) Appl. No.: 10/177,192

(22) Filed: Jun. 21, 2002

(65) Prior Publication Data

US 2003/0235906 A1 Dec. 25, 2003

(51) Int. Cl.
*C12M 1/34* (2006.01)

(52) U.S. Cl. ............................... 435/287.2; 435/288.3; 435/288.4

(58) Field of Classification Search ............. 435/287.2, 435/288.3, 288.4, 288.7, 810, 91.2; 422/101, 422/102

See application file for complete search history.

(56) References Cited

U.S. PATENT DOCUMENTS

| | | | |
|---|---|---|---|
| 4,834,946 A | | 5/1989 | Levin |
| 5,192,503 A | * | 3/1993 | McGrath et al. ............... 422/57 |
| 5,945,334 A | | 8/1999 | Besemer et al. |
| 6,258,593 B1 | | 7/2001 | Schembri et al. |
| 6,309,889 B1 | | 10/2001 | Cutler et al. |
| 6,399,394 B1 | | 6/2002 | Dahm et al. |
| 2003/0231985 A1 | | 12/2003 | Schleifer |
| 2003/0232344 A1 | | 12/2003 | Schleifer et al. |

FOREIGN PATENT DOCUMENTS

WO     WO 95/27196     10/1995

OTHER PUBLICATIONS

Communication European Patent Office dated Sep. 25, 2003, EP Search Report for EP 03253932 dated Sep. 18, 2003, counterpart of U.S. Appl. No. 10/177,192.

* cited by examiner

*Primary Examiner*—David Redding

(57) ABSTRACT

Devices and methods for assaying a sample for the presence of at least one analyte are provided. The subject compression devices include a base and a cover configured to apply a compression force to a structure comprising a first substrate separated from a second substrate by a separator when present in the device. The subject methods include contacting a sample with a first surface of a first substrate to produce a substrate supported sample, placing the substrate supported sample in contact with a second substrate to form a structure that includes the first and second substrates spaced-apart from each other by a separator, wherein one of the substrates is an array substrate having at least one array, applying a compression force to compress the structure together using a compression device and reading the at least one array to obtain a result.

11 Claims, 16 Drawing Sheets

FIG. 4
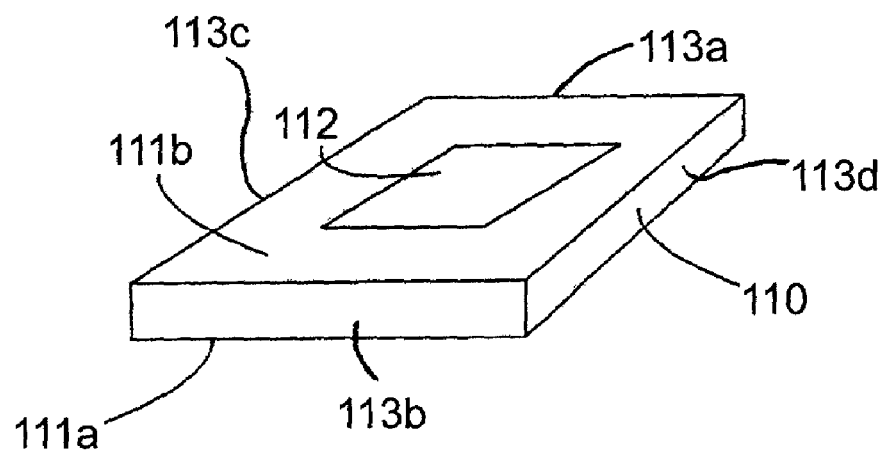
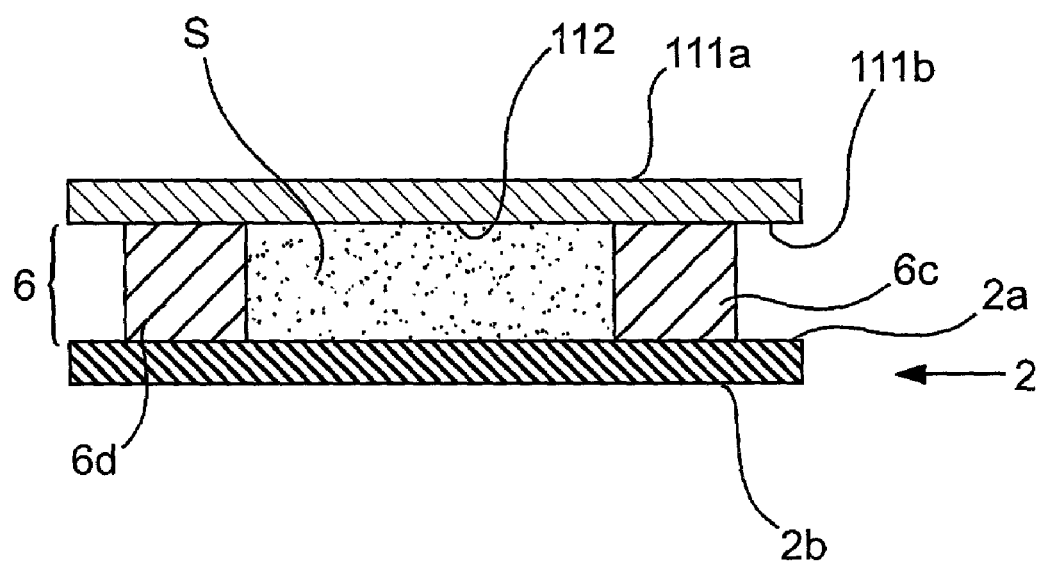
FIG. 5

DEVICES AND METHODS FOR PERFORMING ARRAY BASED ASSAYS

FIELD OF THE INVENTION

The field of this invention is biopolymeric arrays.

BACKGROUND OF THE INVENTION

Array assays between surface bound binding agents or probes and target molecules in solution may be used to detect the presence of particular biopolymers. The surface-bound probes may be oligonucleotides, peptides, polypeptides, proteins, antibodies or other molecules capable of binding with target molecules in solution. Such binding interactions are the basis for many of the methods and devices used in a variety of different fields, e.g., genomics (in sequencing by hybridization, SNP detection, differential gene expression analysis, identification of novel genes, gene mapping, finger printing, etc.) and proteomics.

One typical array assay method involves biopolymeric probes immobilized in an array on a substrate such as a glass substrate or the like. A solution containing analytes that bind with the attached probes is placed in contact with the array substrate, covered with another substrate such as a coverslip or the like to form an assay area and placed in an environmentally controlled chamber such as an incubator or the like. Usually, the targets in the solution bind to the complementary probes on the substrate to form a binding complex. The pattern of binding by target molecules to biopolymer probe features or spots on the substrate produces a pattern on the surface of the substrate and provides desired information about the sample. In most instances, the target molecules are labeled with a detectable tag such as a fluorescent tag, chemiluminescent tag or radioactive tag. The resultant binding interaction or complexes of binding pairs are then detected and read or interrogated, for example by optical means, although other methods may also be used. For example, laser light may be used to excite fluorescent tags, generating a signal only in those spots on the biochip that have a target molecule and thus a fluorescent tag bound to a probe molecule. This pattern may then be digitally scanned for computer analysis.

As will be apparent, control of the assay environment and conditions contributes to increased reliability and reproducibility of the array assays. However, merely placing a substrate such as a coverslip over the array, as is commonly done, is often insufficient to allow precise control over the assay and permits leakage and evaporation of sample from the array site, where in many instances the quantity of sample is extremely limited.

During an array assay such as a hybridization assay, the assay is often performed at elevated temperatures and care must be taken so that the array does not dry out. Simply positioning a second slide over the array allows contents to leak or dry out during use, adversely impacting the assay. In addition, the substrate carrying the array cannot be tipped or moved from the horizontal position without risk that the substrate or cover slip will slip off. Maintaining the array in a humid environment may reduce drying-out, but offers only an incomplete solution.

Various closeable chambers or containers have been developed for conducting array-based assays which attempt to solve the problem of sample evaporation. However, many of these chambers fail to provide a complete seal around the array assay area. As such, leakage and evaporation of contents from the chamber still exists in these chambers. Furthermore, many of these chambers are complex and have numerous components that must be assembled by the user. Due to this complexity, the assembly process is often time-consuming and labor intensive.

Thus, there continues to be an interest in the development of new devices for array-based assays and methods of using the same. Of particular interest is the development of an array assay device, and methods of use thereof, that provides a fluid barrier around the assay area to prevent leakage and evaporation from the array assay area, is easy to assemble and use, includes a minimum of components, and that may also be capable of testing multiple samples with multiple arrays without cross-contamination.

SUMMARY OF THE INVENTION

Devices and methods for assaying a sample for the presence of at least one analyte are provided. The subject compression devices include a base and a cover configured to apply a compression force to a structure comprising a first substrate spaced-apart from a second substrate by a separator when present in the device.

The subject methods include contacting a sample with a first surface of a first substrate to produce a substrate supported sample, placing the substrate supported sample in contact with a second substrate to form a structure that includes the first and second substrates spaced-apart from each other by a separator, wherein one of the substrates is an array substrate having at least one array, applying a compression force to compress the structure together using a compression device that includes a base and a cover configured to apply a compression force to the structure when present in the compression device and reading the at least one array to obtain a result.

Also provided are systems and kits for use in practicing the subject methods. The subject methods and devices find use in any array-based application, including genomic and proteomic applications.

BRIEF DESCRIPTIONS OF THE DRAWINGS

FIG. 4 shows an exemplary substrate carrying an array, such as may be used in the devices of the subject invention.

FIG. 5 shows a cross-sectional a view of a backing element supported sample joined with a substrate having at least one array to provide a sealed assay area around the array.

Figure 6A:
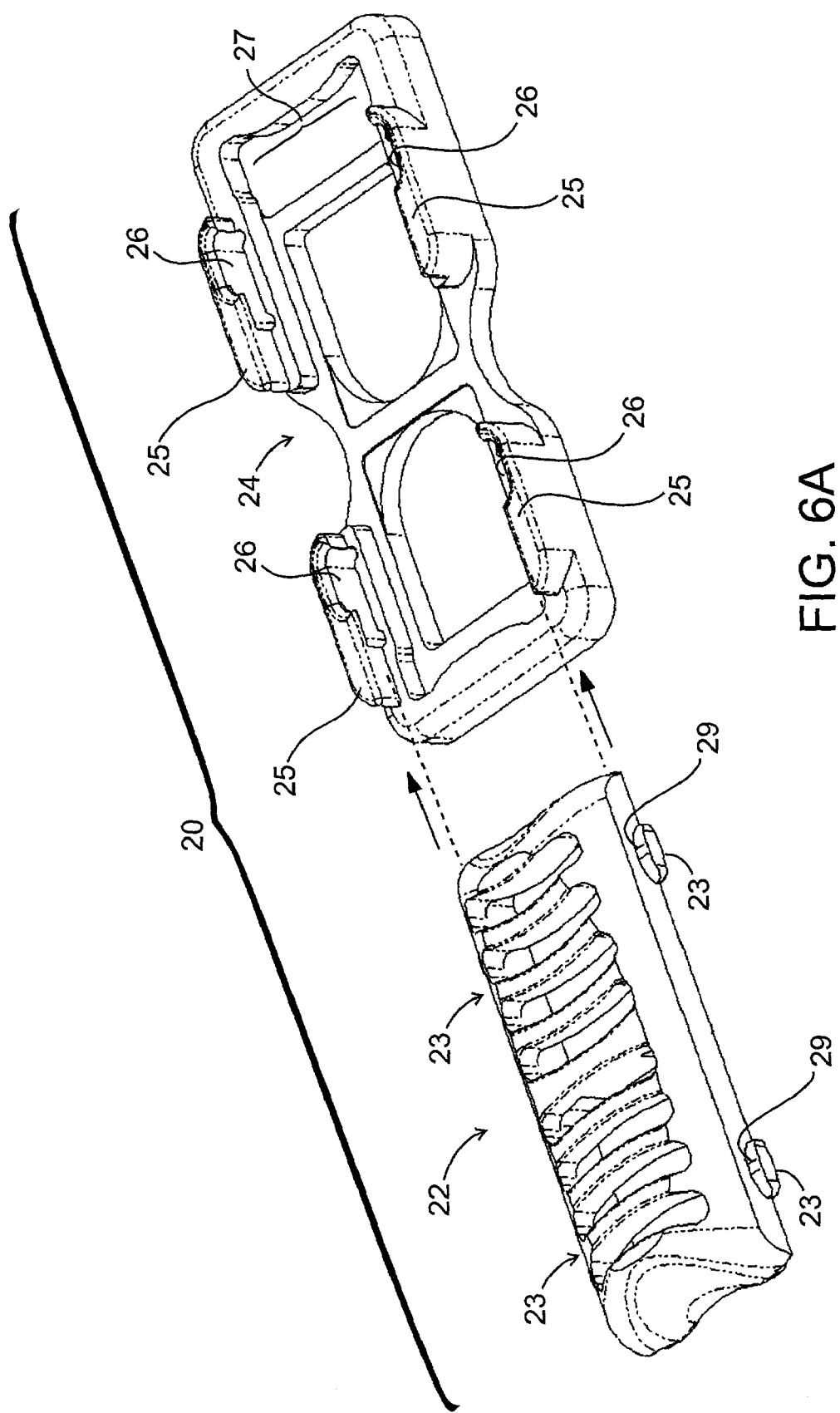
Figure 6B:
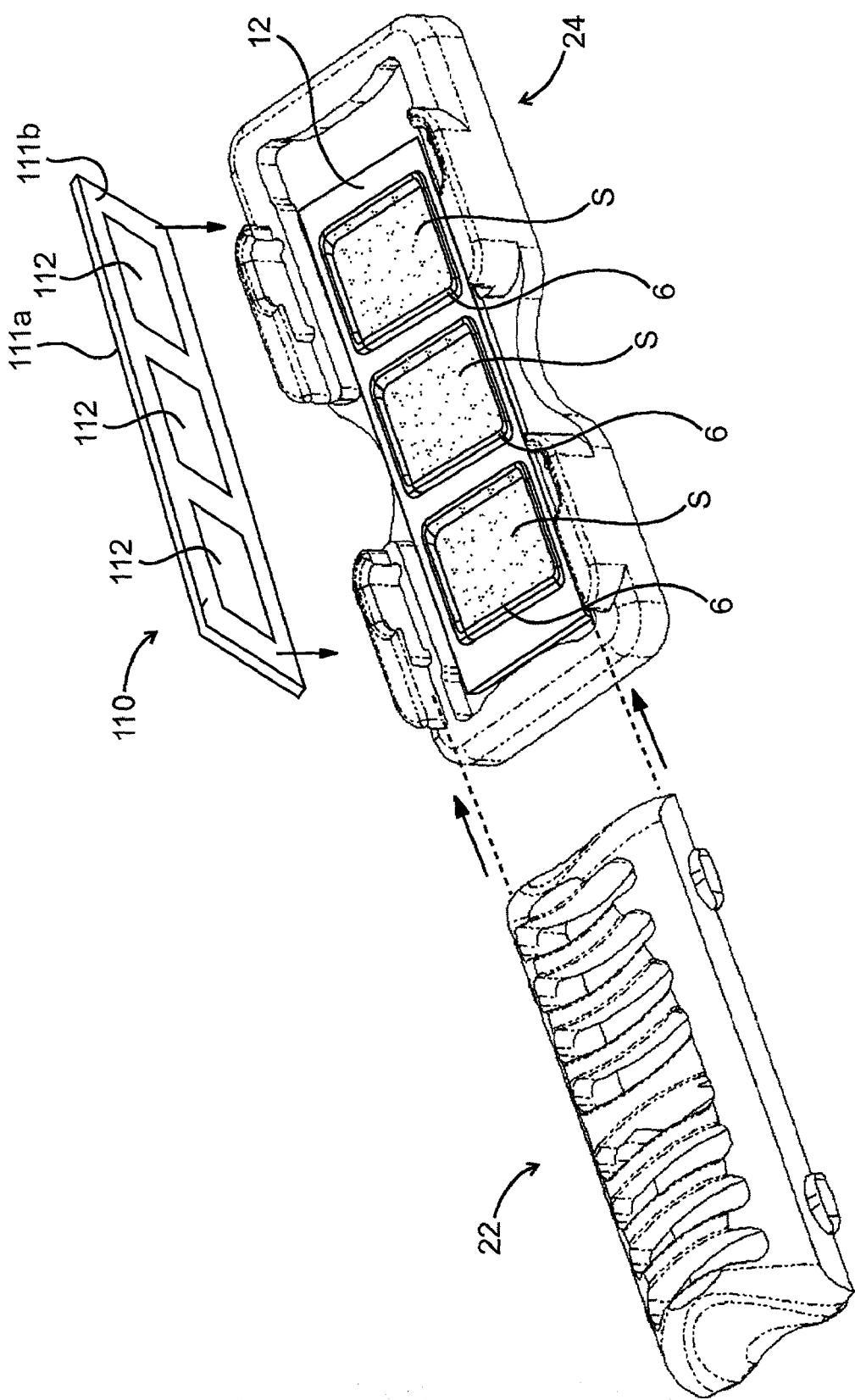
Figure 6C:
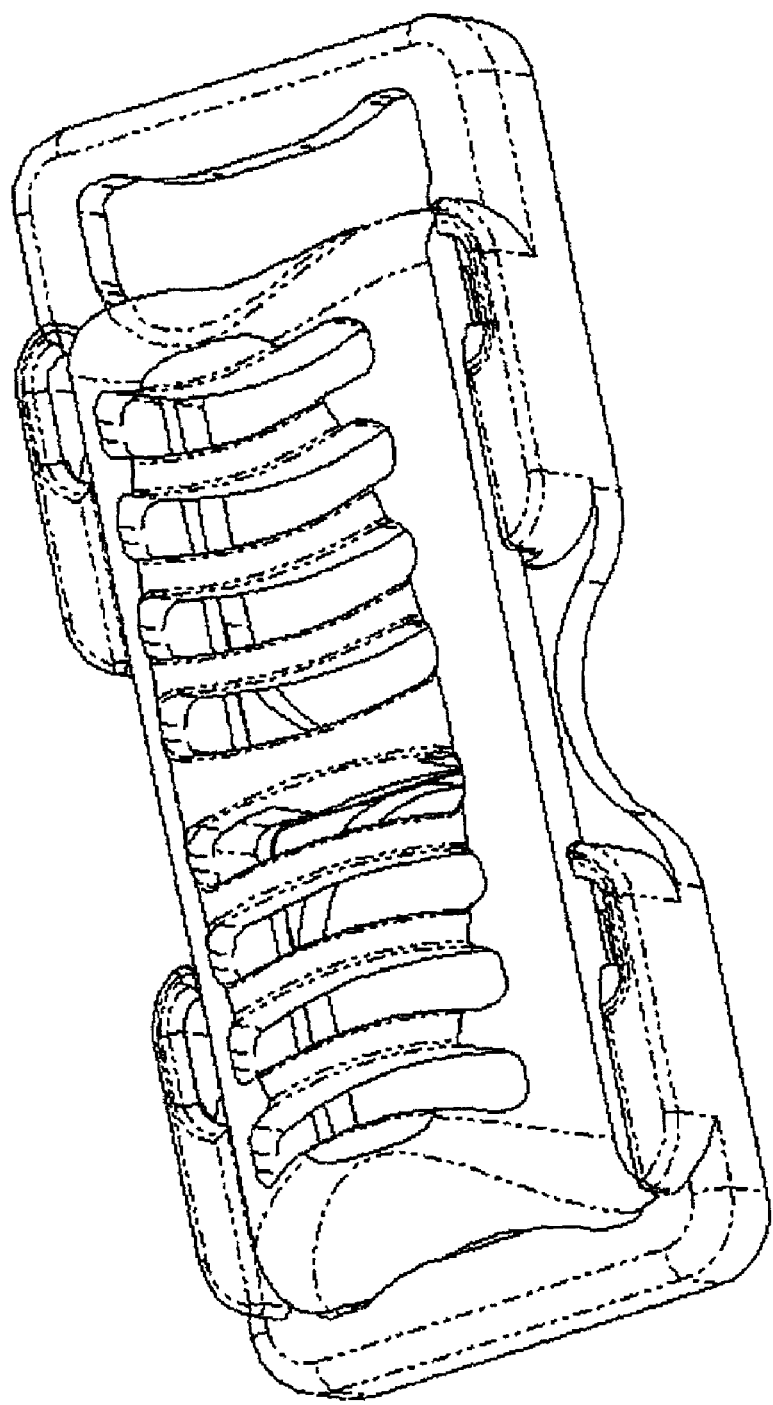

FIG. 6A shows an exploded view of a slideably engageable compression device according to the subject invention. FIG. 6B shows an exploded view of the device of FIG. 6A having a backing element supported sample positioned therein and an array substrate ready to be contacted with the backing element supported sample. FIG. 6C shows the device of FIG. 6A in a closed or assembled configuration.

Figure 7A:
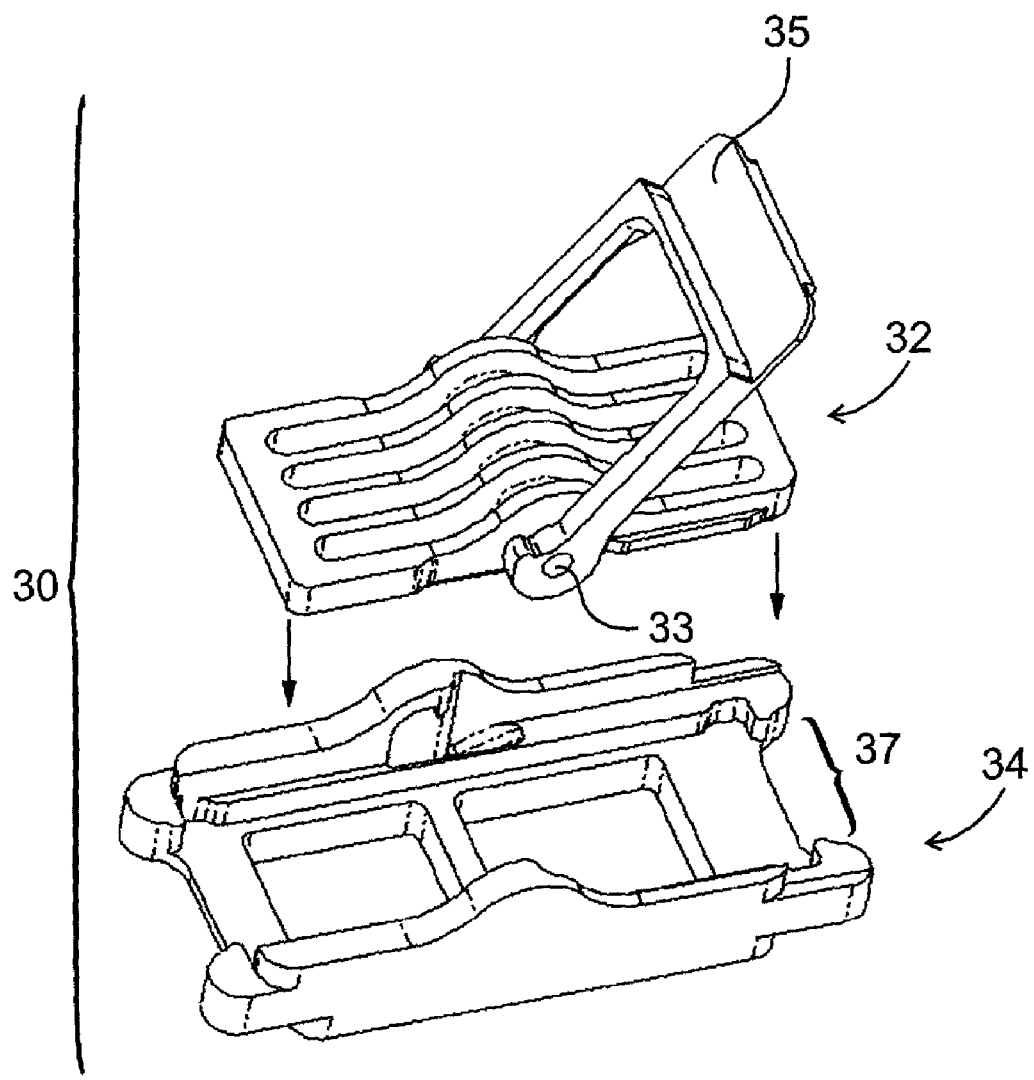
Figure 7B:
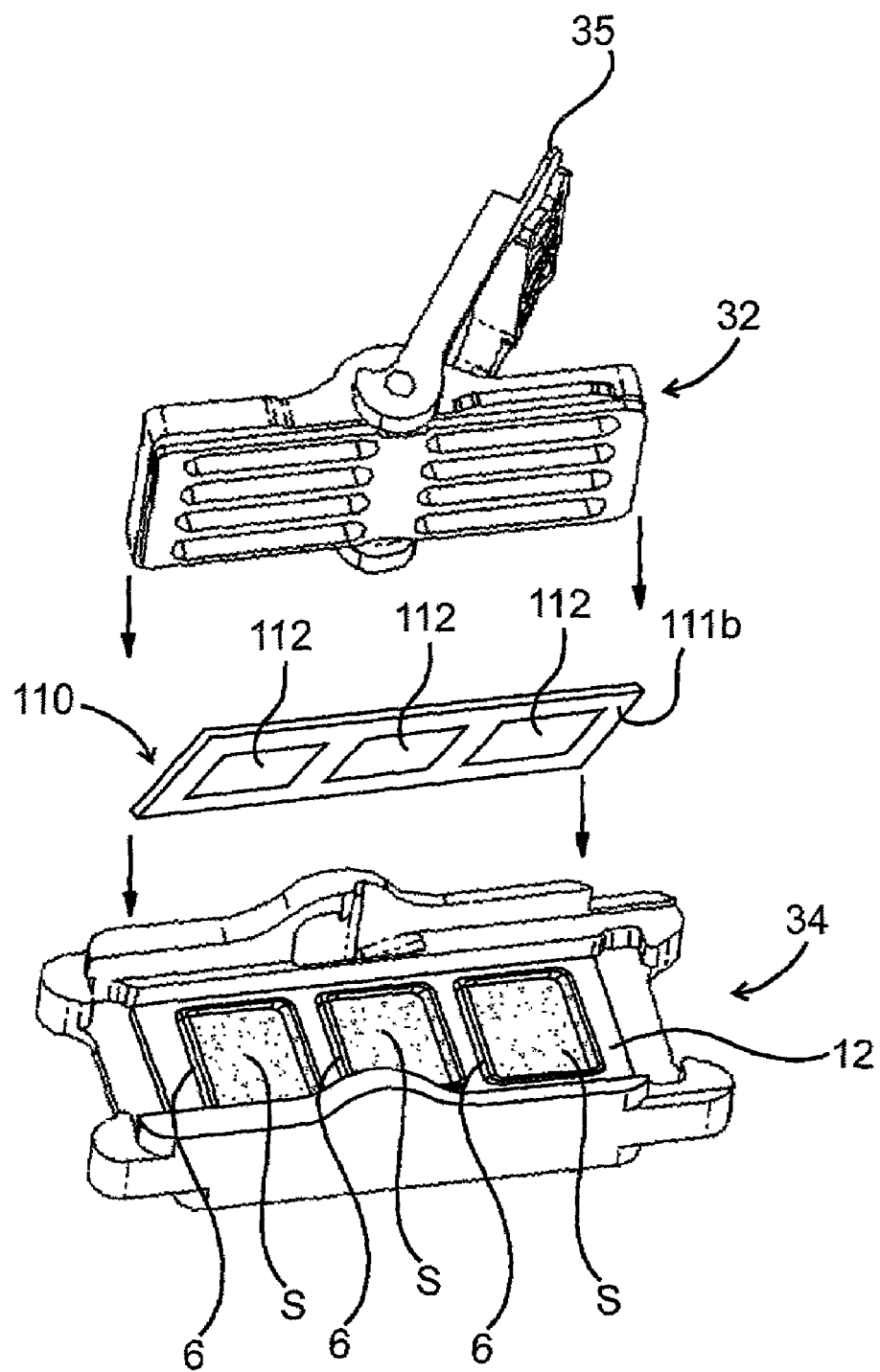
Figure 7C:
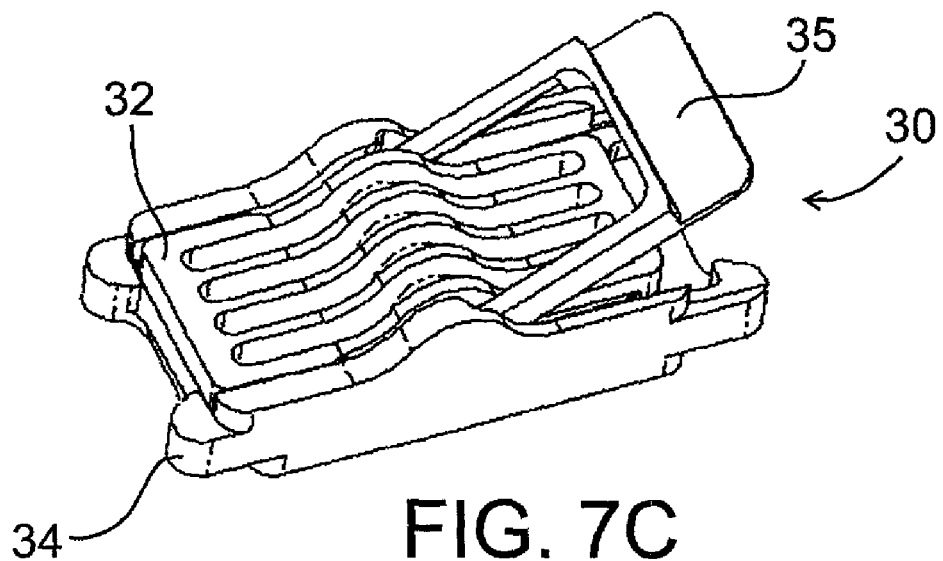
Figure 7D:
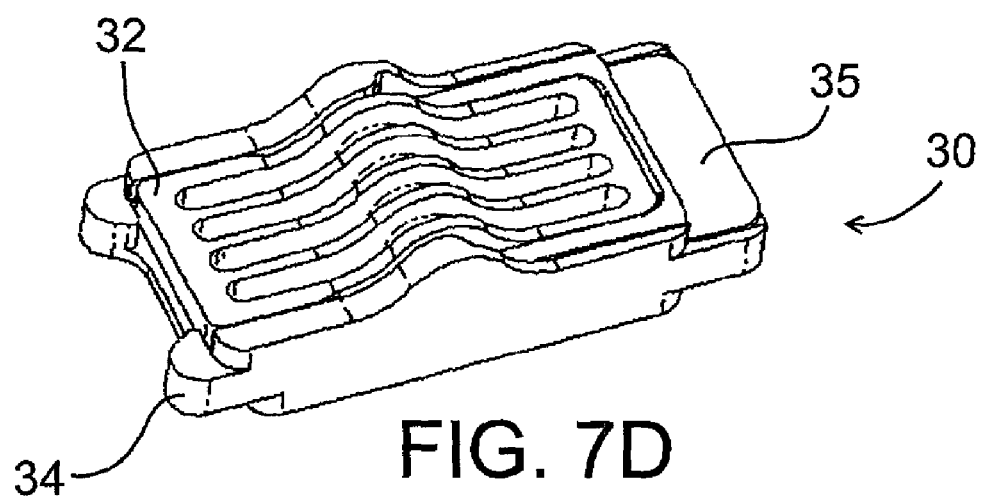

FIG. 7A shows an exploded view of a cam compression device according to the subject invention. FIG. 7B shows an exploded view of the device of FIG. 7A having a backing element supported sample positioned therein and an array substrate ready to be contacted with the backing element supported sample and a cover ready to be engaged with the base. FIG. 7C shows the device of FIG. 7A in a closed configuration, prior to application of compression (cam lever up). FIG. 7D shows the device of FIG. 7C following the application of compression (cam lever down).

Figures 8A, 8C:
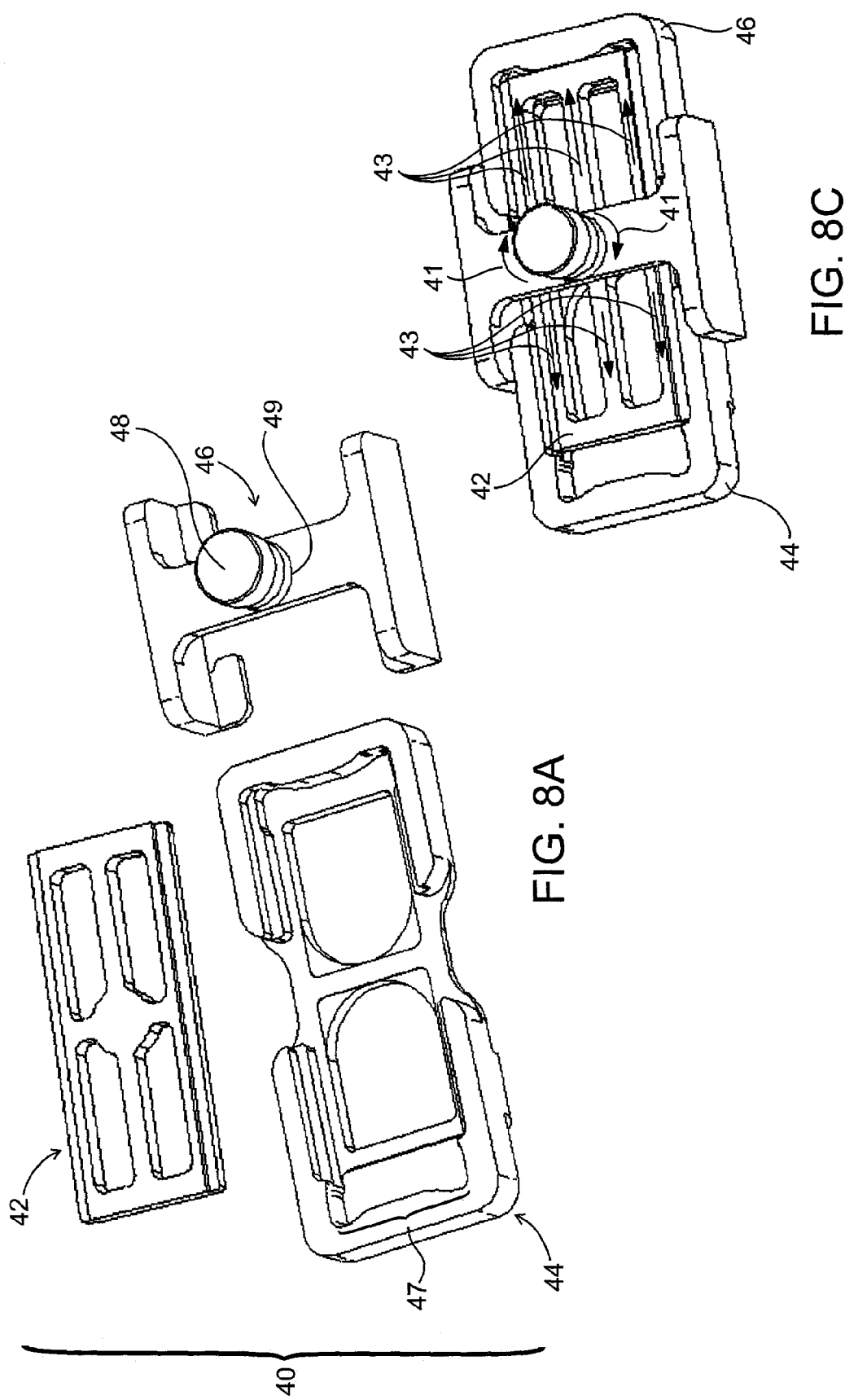
Figure 8B:
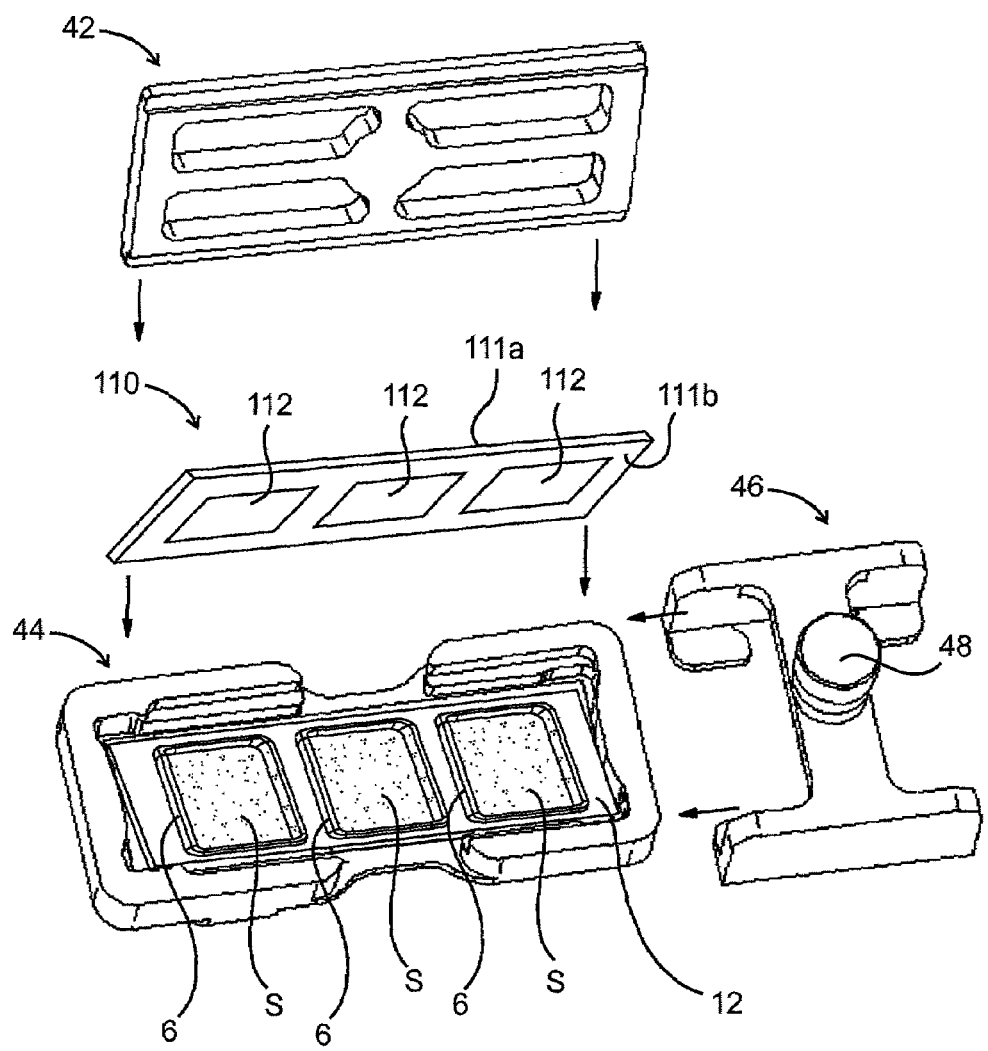

FIG. 8A shows an exploded view of a slide-bridge compression device according to the subject invention. FIG. 8B shows an exploded view of the device of FIG. 8A having a backing element supported sample positioned therein, an array substrate ready to be contacted with the backing element supported sample, a cover ready to be engaged with the base and a slide bridge ready to be slid over the engaged base and cover. FIG. 8C shows the device of FIG. 8A in a closed or assembled configuration.

Figure 9A:
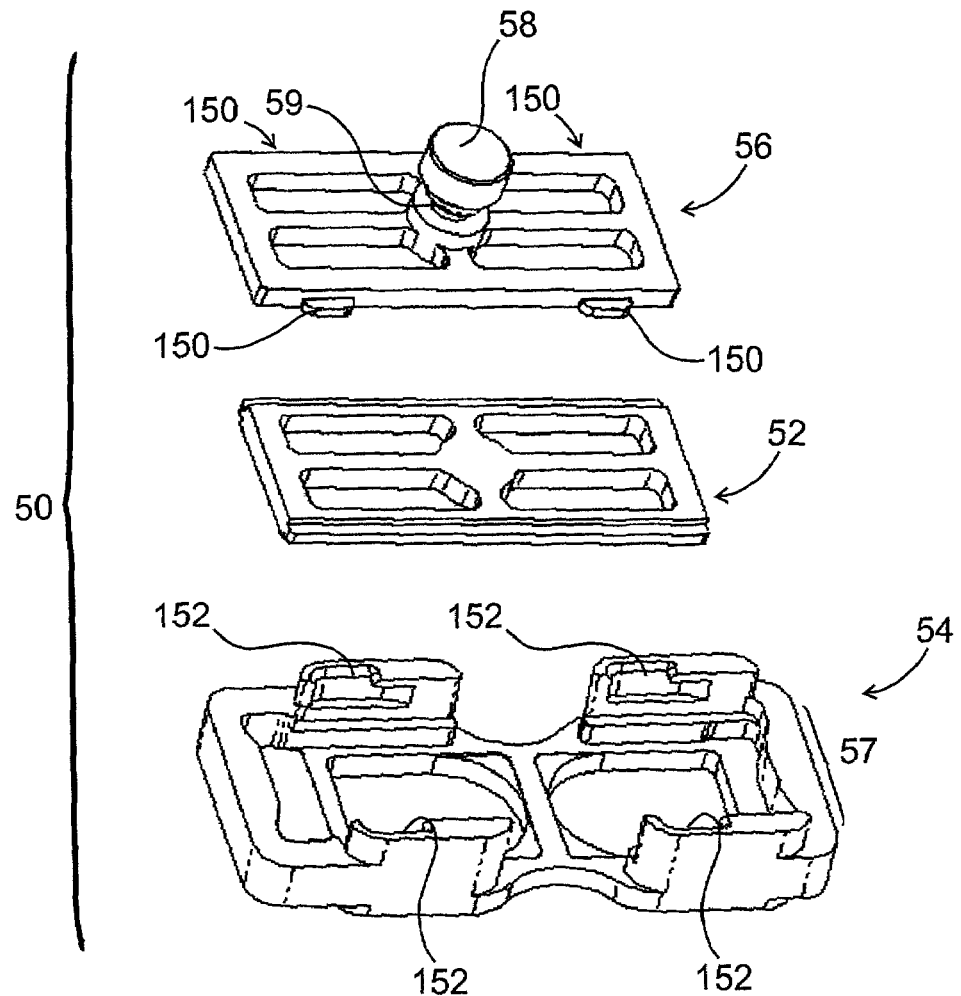
Figure 9C:
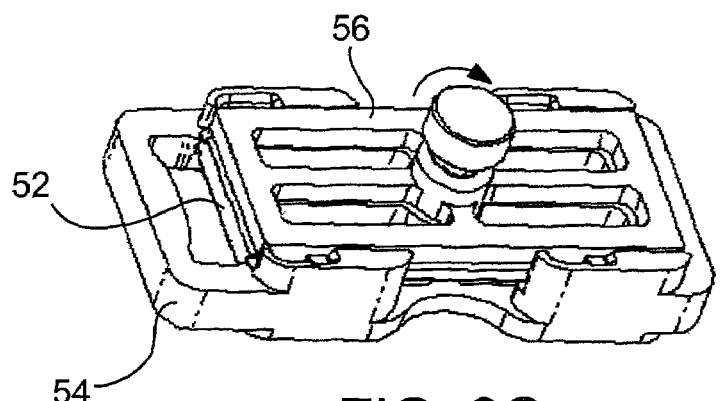
Figure 9B:
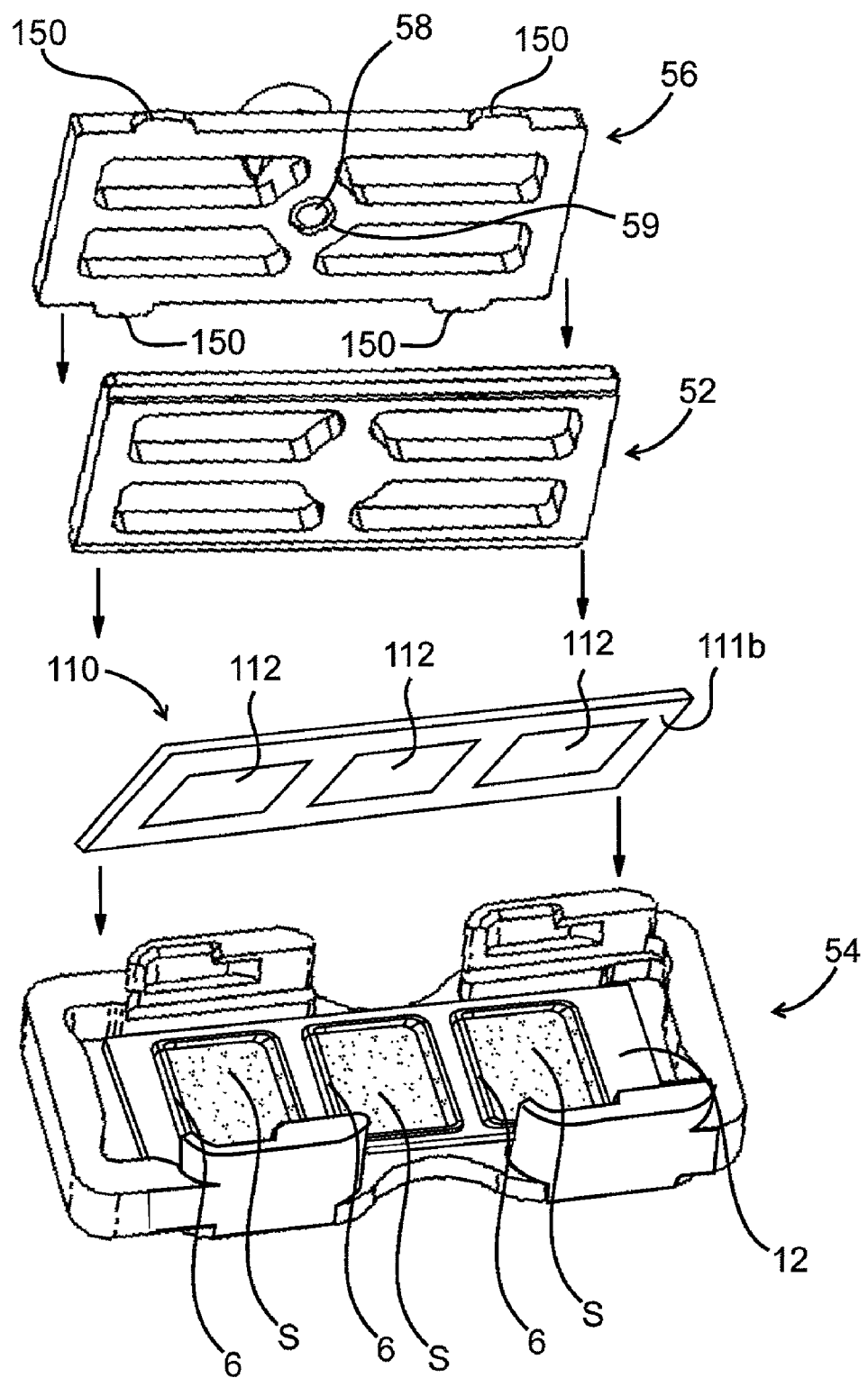

FIG. 9A shows an exploded view of an insert bracket compression device according to the subject invention. FIG. 9B shows an exploded view of the device of FIG. 9A having a backing element supported sample positioned therein, an array substrate ready to be contacted with the backing element supported sample, a cover ready to be engaged with the base and an insert bracket ready to be inserted over the engaged base and cover. FIG. 9C shows the device of FIG. 9A in a closed or assembled configuration.

Figure 10B:
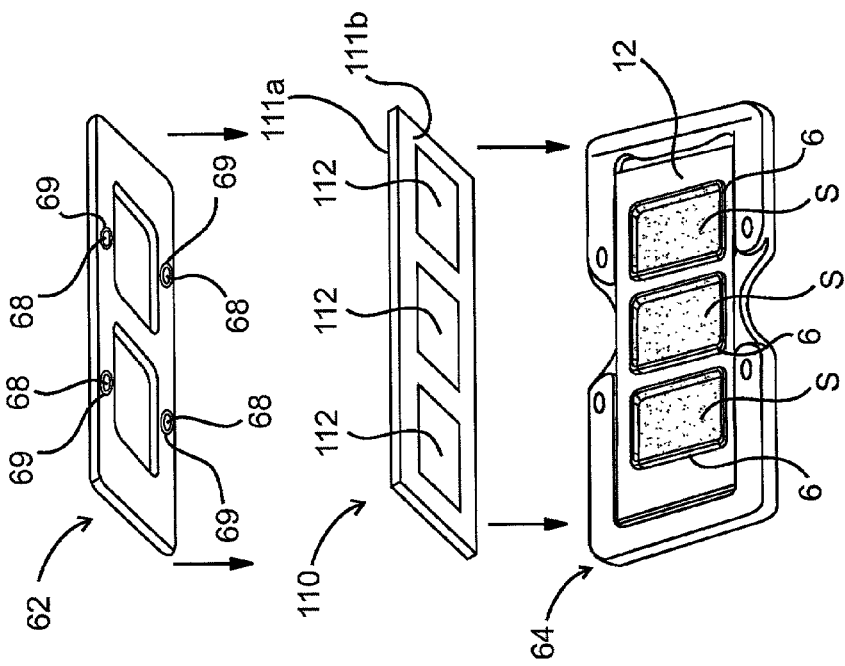
Figure 10A:
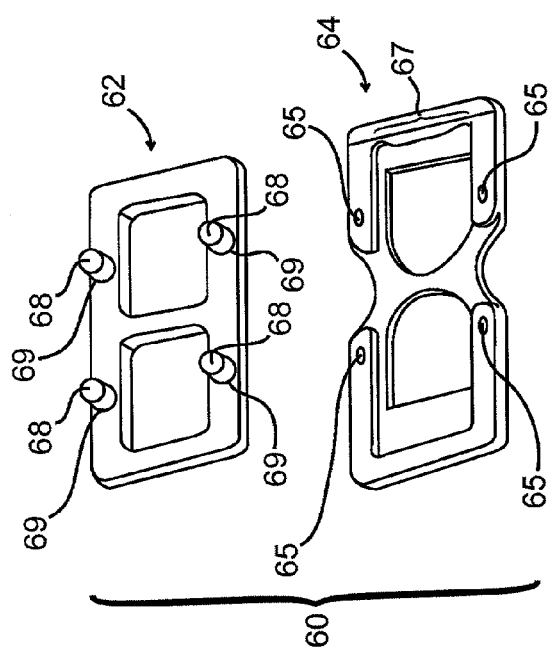
Figure 10C:
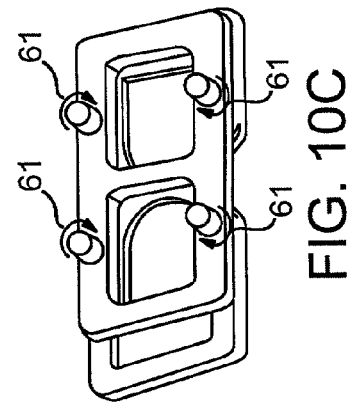

FIG. 10A shows an exploded view of a multi-point compression device according to the subject invention. FIG. 10B shows an exploded view of the device of FIG. 10A having a backing element supported sample positioned therein, an array substrate ready to be contacted with the backing element supported sample and the multi point cover ready to be engaged with the base. FIG. 10C shows the device of FIG. 10A in a closed or assembled configuration.

Figure 11:
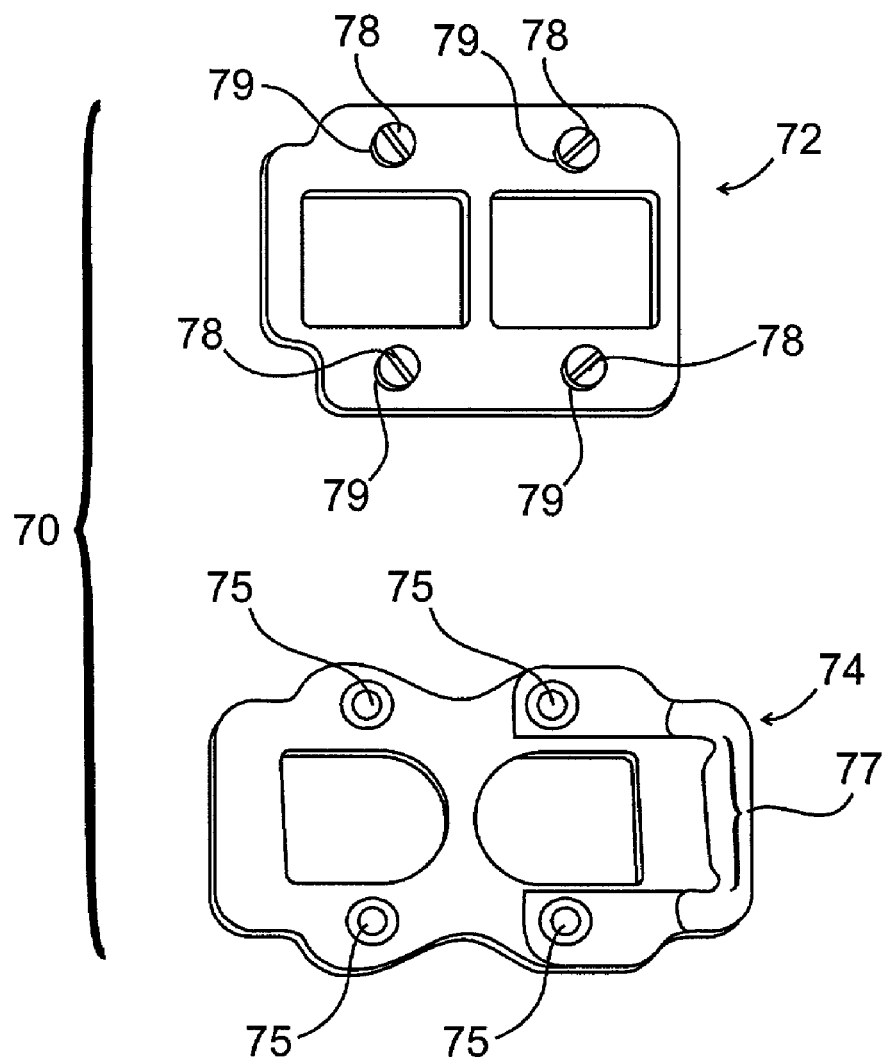

FIG. 11 shows an exploded view of a quarter turn compression device according to the subject invention.

Figure 12:
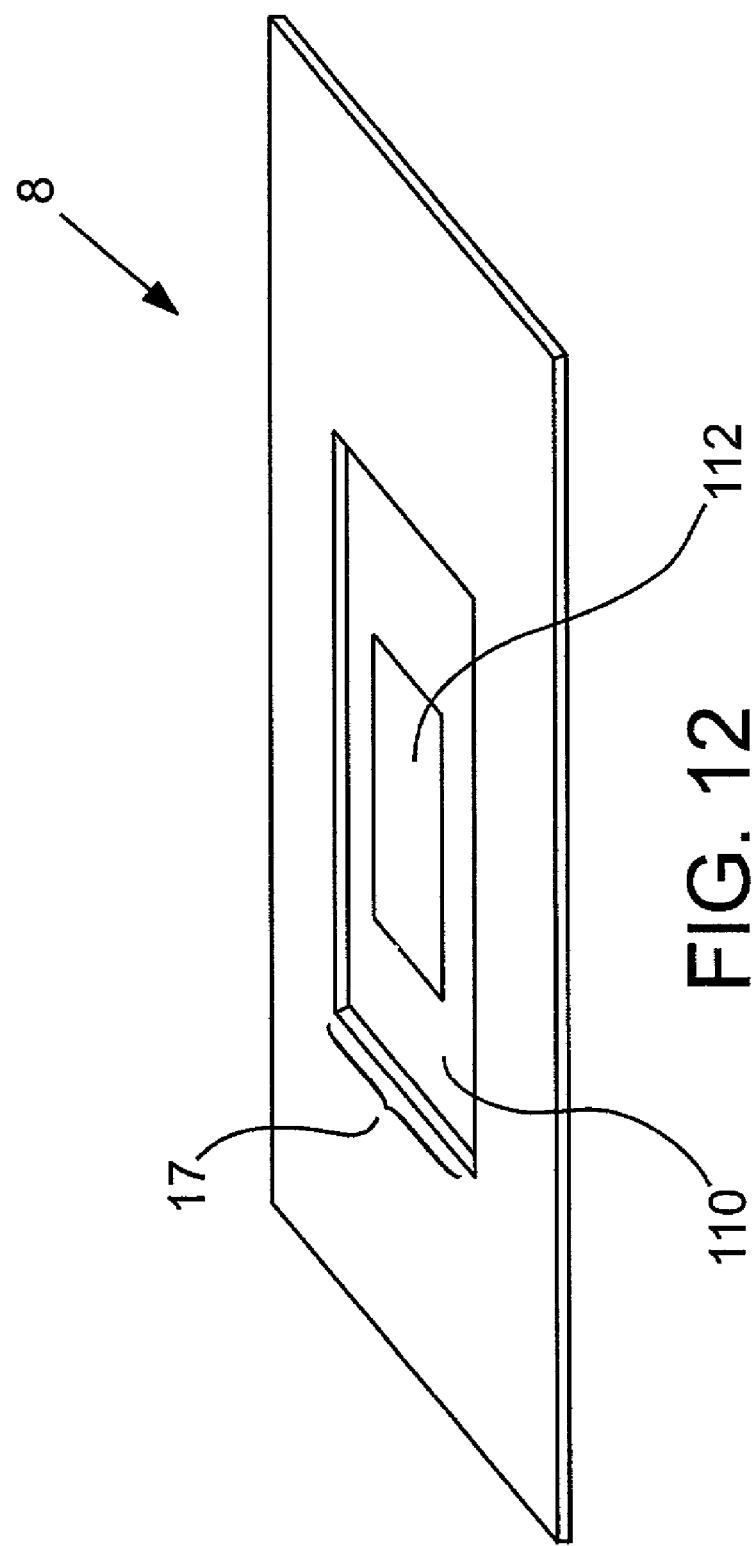

FIG. 12 shows an exemplary embodiment of a substrate receiving frame.

Figure 13:
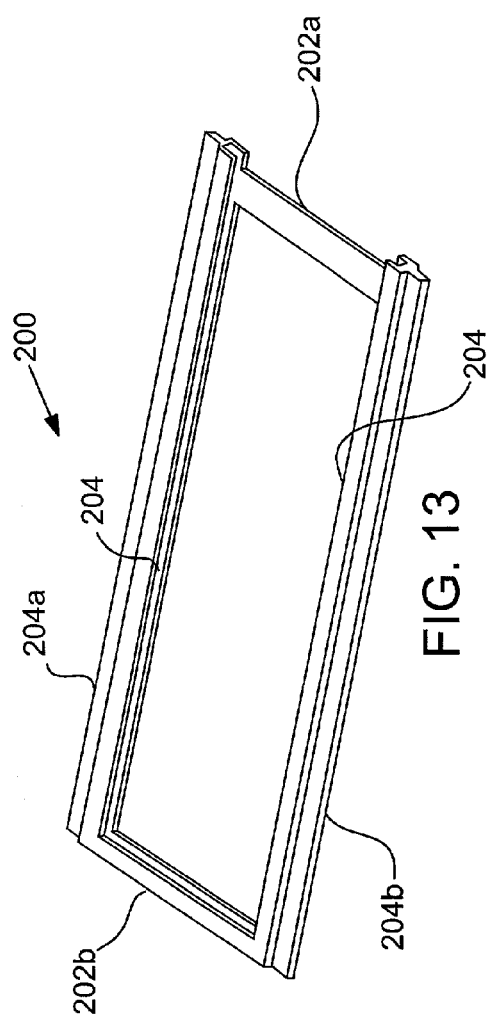

FIG. 13 shows an exemplary embodiment of an array holder.

Figure 14:
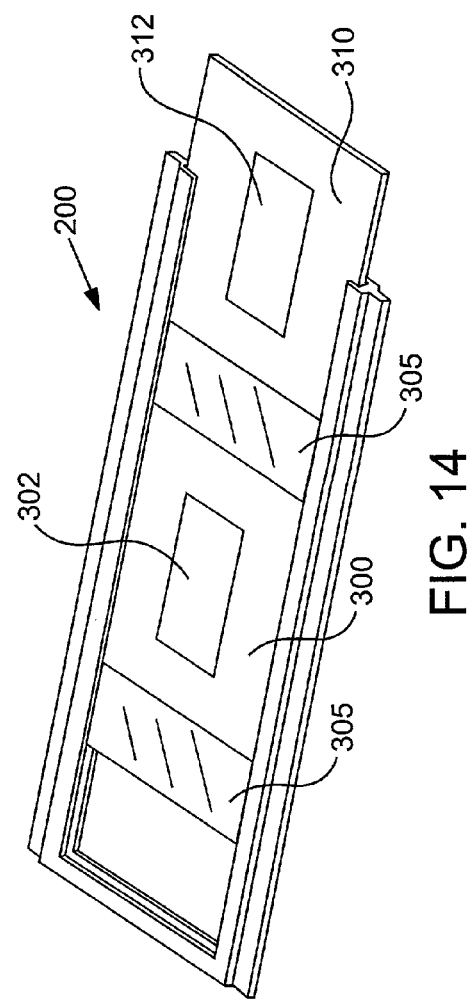

FIG. 14 shows an array holder according to the subject invention holding arrays.

DEFINITIONS

The term "polymer" refers to any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "monomer" as used herein refers to a chemical entity that can be covalently linked to one or more other such entities to form an oligomer. Examples of monomers include nucleotides, amino acids, saccharides, peptides, and the like. In general, the monomers used in conjunction with the present invention have first and second sites (e.g., C-termini and N-termini, or 5' and 3' sites) suitable for binding to other like monomers by means of standard chemical reactions (e.g., condensation, nucleophilic displacement of a leaving group, or the like), and a diverse element which distinguishes a particular monomer from a different monomer of the same type (e.g., an amino acid side chain, a nucleotide rigid bottom cover surface, etc.). The initial substrate-bound monomer is generally used as a building-block in a multi-step synthesis procedure to form a complete ligand, such as in the synthesis of oligonucleotides, oligopeptides, and the like.

The term "oligomer" is used herein to indicate a chemical entity that contains a plurality of monomers. As used herein, the terms "oligomer" and "polymer" are used interchangeably. Examples of oligomers and polymers include, but are not limited to: polydeoxyribonucleotides, polyribonucleotides, other polynucleotides which are B or C-glycosides of a purine or pyrimidine rigid bottom cover surface, polypeptides, polysaccharides, and other chemical entities that contain repeating units of like chemical structure.

The term "ligand" as used herein refers to a moiety that is capable of covalently or otherwise chemically binding a compound of interest. The ligand may be a portion of the compound of interest. The term "ligand" in the context of the invention may or may not be an "oligomer" as defined above. The term "ligand" as used herein may also refer to a compound that is synthesized on the substrate surface as well as a compound is "pre-synthesized" or obtained commercially, and then attached to the substrate surface.

The terms "array," "biopolymeric array" and "biomolecular array" are used herein interchangeably to refer to an arrangement of ligands or molecules of interest on a substrate surface, which can be used for analyte detection, combinatorial chemistry, or other applications wherein a two-dimensional arrangement of molecules of interest can be used. That is, the terms refer to an ordered pattern of probe molecules adherent to a substrate, i.e., wherein a plurality of molecular probes are bound to a substrate surface and arranged in a spatially defined and physically addressable manner. Such arrays may be comprised of oligonucleotides, peptides, polypeptides, proteins, antibodies, or other molecules used to detect sample molecules in a sample fluid.

The term "biomolecule" means any organic or biochemical molecule, group or species of interest that may be formed in an array on a substrate surface. Exemplary biomolecules include peptides, proteins, amino acids and nucleic acids.

The term "peptide" as used herein refers to any compound produced by amide formation between a carboxyl group of one amino acid and an amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "nucleic acid" as used herein means a polymer composed of nucleotides, e.g., deoxyribonucleotides or ribonucleotides, or compounds produced synthetically (e.g. PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA"s used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "polynucleotide" as used herein refers to single or double stranded polymer composed of nucleotide monomers of generally greater than 100 nucleotides in length.

The term "sample" as used herein relates to a material or mixture of materials, typically, although not necessarily, in fluid form, containing one or more components of interest.

The terms "nucleoside" and "nucleotide" are intended to include those moieties which contain not only the known purine and pyrimidine rigid bottom cover surfaces, but also other heterocyclic rigid bottom cover surfaces that have been modified. Such modifications include methylated purines or pyrimidines, acylated purines or pyrimidines, or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "chemically inert" is used herein to mean the chemical structure is substantially unchanged by contact with reagents and conditions normally involved in array based assays such as hybridization reactions or any other related reactions or assays, e.g., proteomic array applications.

The term "communicating" information refers to transmitting data representing that information as electrical signals over a suitable communication channel (for example, a private or public network).

The term "forwarding" an item refers to any means of getting that item from one location to the next, whether by physically transporting that item or otherwise (where that is possible) and includes, at least in the case of data, physically transporting a medium carrying the data or communicating the data.

The term "physically inert" is used herein to mean the physical structure is substantially unchanged by contact with reagents and conditions normally involved in array based assays such as hybridization reactions or any other related assays or reactions.

The terms "target" "target molecule" and "analyte" are used herein interchangeably and refer to a known or unknown molecule in a sample, which will hybridize to a molecular probe on a substrate surface if the target molecule and the molecular probe contain complementary regions, i.e., if they are members of a specific binding pair. In general, the target molecule is a biopolymer, i.e., an oligomer or polymer such as an oligonucleotide, a peptide, a polypeptide, a protein, and antibody, or the like.

The term "hybridization" as used herein refers to binding between complementary or partially complementary molecules, for example as between the sense and anti-sense strands of double-stranded DNA. Such binding is commonly non-covalent binding, and is specific enough that such binding may be used to differentiate between highly complementary molecules and others less complementary. Examples of highly complementary molecules include complementary oligonucleotides, DNA, RNA, and the like, which comprise a region of nucleotides arranged in the nucleotide sequence that is exactly complementary to a probe; examples of less complementary oligonucleotides include ones with nucleotide sequences comprising one or more nucleotides not in the sequence exactly complementary to a probe oligonucleotide.

The term "hybridization solution" or "hybridization reagent" used herein interchangeably refers to a solution suitable for use in a hybridization reaction.

The terms "mix" and "mixing" as used herein means to cause fluids to flow within a volume so as to more uniformly distribute solution components, as after different solutions are combined or after a solution is newly introduced into a volume or after a component of the solution is locally depleted.

The term "probe" as used herein refers to a molecule of known identity adherent to a substrate.

The term "remote location" refers to a location other than the location at which the array is present and hybridization occur. As such, when one item is indicated as being "remote" from another, what is meant is that the two items are at least in different buildings, and may be at least one mile, ten miles, or at least one hundred miles apart.

The term "sealing element" is used herein to refer to any sealing device or structure that produces a seal between two surfaces, such as a gasket, a lip, material interface, ledge or ridge, viscous sealant, or the like.

The term "stringent hybridization conditions" as used herein refers to conditions that are that are compatible to produce duplexes on an array surface between complementary binding members, i.e., between probes and complementary targets in a sample, e.g., duplexes of nucleic acid probes, such as DNA probes, and their corresponding nucleic acid targets that are present in the sample, e.g., their corresponding mRNA analytes present in the sample. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

DETAILED DESCRIPTION OF THE INVENTION

Devices and methods for assaying a sample for the presence of at least one analyte are provided. The subject compression devices include a base and a cover configured to apply a compression force to a structure comprising a first substrate separated from a second substrate by a separator when present in the device.

The subject methods include contacting a sample with a first surface of a first substrate to produce a substrate supported sample, placing the substrate supported sample in contact with a second substrate to form a structure that includes the first and second substrates spaced-apart from each other by a separator, wherein one of the substrates is an array substrate having at least one array, applying a compression force to compress the structure together using a compression device that includes a base and a cover configured to apply a compression force to the structure when present in the compression device and reading the at least one array to obtain a result.

Also provided are systems and kits for use in practicing the subject methods. The subject methods and devices find use in any array-based application, including genomic and proteomic applications.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an array" includes a plurality of such arrays and reference to "the fluid barrier" includes reference to one or more fluid barriers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Introduction

As summarized above, the subject invention provides devices and methods for performing array-based assays, i.e., array binding assays. The subject invention can be used with a number of different types of arrays in which a plurality of distinct polymeric binding agents (i.e., of differing sequence) are stably associated with at least one surface of a substrate or solid support. The polymeric binding agents may vary widely, however polymeric binding agents of particular interest include peptides, proteins, nucleic acids, polysaccharides, synthetic mimetics of such biopolymeric binding agents, etc. In many embodiments of interest, the biopolymeric arrays are arrays of nucleic acids, including oligonucleotides, polynucleotides, cDNAs, mRNAs, synthetic mimetics thereof, and the like.

While the subject devices and methods find use in array hybridization assays, the subject devices and methods also find use in any suitable binding assay in which members of a specific binding pair interact. That is, any of a number of different binding assays may be performed with the subject devices and methods, where typically a first member of a binding pair is stably associated with the surface of a substrate and a second member of a binding pair is free in a sample, where the binding members may be: ligands and receptors, antibodies and antigens, complementary nucleic acids, and the like. For ease of description only, the subject devices and methods described below will be described primarily in reference to hybridization assays, where such examples are not intended to limit the scope of the invention. It will be appreciated by those of skill in the art that the subject devices and methods may be employed for use with other binding assays as well, such as immunoassays, proteomic assays, etc.

In further describing the subject invention, the subject compression devices are described first in greater detail, followed by a review of the subject methods and representative applications in which the subject methods find use. Finally, kits that find use in practicing the subject methods will be described.

Compression Devices

As summarized above, the subject invention includes compression devices for performing an array assay. The subject compression devices are characterized by a housing that includes a base and a cover configured to apply a compression force to a backing element and array retained therein to force the two together. More specifically, the subject compression devices are dimensioned to fit with a backing element and a substrate having an array, where the backing element and the array are positioned in opposition to each other with at least one container element positioned therebetween, in the compression device. The compression devices of the subject invention apply a compression force to one or both of the backing element and the array substrate to compress the backing element and array substrate together, thereby compressing the one or more container elements "sandwiched" therebetween to provide a substantially vapor and fluid tight assay area around the array formed by the walls of the container element and the opposed surfaces of the backing element array substrate. In certain embodiments, the subject compression devices are configured to apply opposing forces, e.g., equally opposing forces, to the backing element and array substrate to compress them together.

A feature of the subject compression devices is that they are configured to apply a uniform compression force to one or both surfaces of the backing element and array substrate that results in a uniform compression force applied to the container element(s) positioned therebetween (see FIG. 7). In this manner, fluidic contents retained in a container element between a compressed backing element and array substrate are prevented from leaking out and/or evaporating from the container element. Furthermore, because the subject compression devices are configured to provide a substrate supported sample prior to contacting the sample with an array, the subject devices advantageously enable direct sample introduction to this first substrate prior to joining it with a second substrate, which permits sample introduction using a pipette rather than a needle or other sharp-tipped sample introduction element.

Common to all of the subject compression elements is a base member and a mateable cover member that are dimensioned to retain a backing element. In all of the subject compression devices, when the base and the cover are joined together in a closed configuration, they provide a compressive force to one or both of a surface of the backing element and an array substrate to compress them together with at least one separator or container element therebetween.

The compression devices of the subject invention may assume a variety of shapes ranging from simple to complex, with the only limitation being that they are suitably shaped to receive and retain at least one array. The compression devices are usually ergonomically designed for ease-of use and handling. It will be apparent that the shapes of the base and the cover may differ or may be the same. In many embodiments, the compression devices will assume a circular, oval, oblong, square or rectangular shape, although other shapes are possible as well, such as irregular or complex shapes. For example, in those embodiments where at least one array is stably associated with a substrate that is a microscope slide, e.g., a 1"×3" glass microscope slide as is known in the art, the array assay device may have a similar rectangular shape.

The size of the compression devices may vary depending on a variety of factors, including, but not limited to, the size of the array substrate and the like, where the sizes of the base and the cover may differ or may be the same. Generally, the compression devices will be sized to be easily transportable or moveable. In certain embodiments of the subject devices have a substantially rectangular shape, the length of the compression device typically ranges from about 10 mm to about 200 mm, usually from about 20 mm to about 100 mm and more usually from about 50 mm to about 100 mm, the width typically ranges from about 10 mm to about 100 mm, usually from about 20 mm to about 50 mm and more usually from about 40 mm to about 50 mm and the thickness typically ranges from about 2 mm to about 100 mm, usually from about 4 mm to about 50 mm and more usually from about 15 mm to about 35 mm. However, these dimensions are exemplary only and may vary as appropriate.

Accordingly, the subject compression devices are dimensioned such that a backing element/array structure with a separator therebetween may fit in the devices. In other words, a subject compression device has dimensions (length, width and thickness) which enable a backing element and a substrate having at least one array (i.e., a backing element/array structure) to be retained between the base and cover of the compression device when the compression device is in a closed configuration, i.e., the backing element and array would be completely enclosed by the closed compression device. For example, in certain embodiments, the backing element/array structure may have a combined (i.e., total) length that ranges from about 60 mm to about 80 mm, usually from about 70 mm to about 80 mm and more usually from about 74 mm to about 78 mm, a combined width that typically ranges from about 20 mm to about 40 mm, usually from about 24 mm to about 30 mm and more usually from about 25 mm to about 30 mm and a combined thickness that typically ranges from about 0.9 mm to about 4 mm, usually from about 1 mm to about 3.5 mm and more usually from about 1 mm to about 2 mm, where a compression device used with such a backing element/array structure would have the dimensions as described above.

The subject compression devices may be fabricated from a wide variety of materials, with the only limitation being that the material(s) used to fabricate both the base and the cover will not substantially interfere with the assay reagents and will have minimal non-specific binding characteristics, e.g., substantially chemically inert, thermally stable, etc. Specifically, the materials should be chemically and physically stable under conditions employed for the array assay. The material(s) used to fabricate the base may differ from the material(s) used to fabricate the cover or may be the same. Usually, though not always, one or both of the base and/or the cover are rigid or portions thereof are rigid. By rigid it is meant that the base and cover cannot be substantially bent or folded without breaking. Such rigidity enables the device to apply and withstand the compression forces applied thereby. Examples of materials which may be used to fabricate the compression devices include, but are not limited to, plastics such as polytetrafluoroethylene, polypropylene, polystyrene, polycarbonate, PVC, and blends thereof, stainless steel and alloys thereof, siliceous materials, e.g., glasses, fused silica, ceramics and the like. The subject devices or any component thereof may be manufactured to be re-useable or single use. That is, one or more components of the subject compression devices may be reusable while other components may be single use. For example, a base and a cover may be manufactured to be re-useable, while the backing element may be manufactured to be single-use or disposable, or vice versa. Exemplary compression devices will now be described in greater detail in turn. The devices will be described primarily as having a backing element and at least one container as the first substrate that is positioned in the base of the housing, followed by the contact with a second substrate, described primarily as an array substrate having one or more arrays, where this description is for exemplary purposes only and is in no way intended to limit the scope of the invention. It will be apparent that the array may be first positioned in the base, a container element provided thereon and the backing element may then be contacted thereto.

Slideably Engageable Compression Device

FIG. 6A shows an exploded view of an exemplary embodiment of a slideably engageable compression device 20 that includes a base 24 and cover 22 that are slideably engageable or interlockable to provide a closed device. FIG. 6C shows the device of FIG. 6A in an assembled configuration (backing element and array are omitted in FIG. 6C to enable better visualization of the device).

Base 24 include guides or rails 25 on opposing sides of base 24 that are used to guide cover 22 into a closed, lockable position with the base. Guides 25 include locking recesses 26 which are configured to engage mateable locking protrusions 23 with inclined ramps or slopes 29 on cover 22 to apply a compression force to a backing element/array/container structure held in the device. Base 24 also includes substrate positioning area 27 that is dimensioned to retain a substrate such as a backing element or an array substrate (see FIG. 6B). The backing element used in the device may be a separate component or may be integrally formed or molded with the base as a single piece. In use, the first substrate such as a backing element is positioned with the one or more container elements facing the cover or forward, i.e., facing out of the page. The substrate positioning area 27 also retains a second substrate such as an array substrate if the first substrate is a backing element, positioned in opposition to the first substrate and which is contacted with a container element supported sample positioned between the first and second substrates so that the container element(s) are closed on all sides by the fluid barrier walls and the backing element and array substrate. In certain embodiments, the second substrate such as the array is held on the interior or underside of the cover by tabs (not shown), such that when the cover is slideably advanced over the base, the array is simultaneously contacted with the container element supported sample. Alternatively, the second substrate such as an array may be contacted with the container element supported sample by manually placing the array onto the first substrate, e.g., a backing element, before slideably engaging the base and the cover together.

More specifically, a first substrate, e.g., a backing element, is positioned in base 24 with the one or more container elements facing out of the page, as shown in FIG. 6B with backing element 12 having three container elements 6 positioned in base 24. A sample S is contacted with the interiors of the container elements to provide a substrate supported sample. i.e., a container element supported sample. Next, a second substrate having at least one array, shown here as substrate 110 with three arrays 112, is contacted with the container element supported sample such that an enclosed assay area around each array is provided, at which point cover 22 is slideably translated over base 24, using guides 25 and incline ramps 29 to operatively align the cover and the base until locking protrusions 23 on the cover engage with locking recesses 26 on the base, thereby interlocking the base and the cover together in a closed configuration to provide a compression force, as shown in FIG. 6C. The compression force is achieved when the sliding motion of cover 22 is transferred downward or into the page by the interaction of the contacting surfaces between the cover and the base, specifically the contact of the inclined ramps 29 located on the locking protrusions 23 of cover 22 and the locking recesses 26 of base 24. As mentioned above, contacting the array with the container element supported sample and slideably engaging the cover may be accomplished simultaneously.

The locking engagement of the base and the cover uniformly applies a compression force downward or rearward, i.e., into the page, to compress the backing element and the array substrate together, thereby providing a compression force to the container element(s) positioned between the backing element and the array substrate. In other words, the compression force that is applied by the subject compression device is uniformly applied to the "footprint" of the container elements. Such compression produces a substantially vapor and fluid tight seal or assay area around the one or more arrays on the array substrate.

Cam Compression Device

FIGS. 8A-8d show an exemplary embodiment of a cam compression device according to the subject methods. FIG. 8A shows an exploded view of cam compression device 30 that includes base 34 and cover 32 that is interlockable to base 34 to form a closed device, as shown in the assembled views of cam device 30 in FIGS. 8C and 8D. Cam compression device 30 is configured to apply a compression force by the actuation of cam lever 35, operatively associated with cam pivot 33. Base 34 includes substrate positioning area 37 that is dimensioned to retain a substrate such as a backing element or array substrate. A backing element used in the device may be a separate component or may be integrally formed or molded with the base as a single piece. In use, a first substrate such as a backing element is positioned with the one or more container elements facing the cover or forward, i.e., facing out of the page. The substrate positioning area also retains a second substrate such as an array substrate if the first substrate is a backing element, positioned in opposition to the first substrate and which is contacted with a container element supported sample positioned between the first and second substrates so that the container element(s) are closed on all sides by the fluid barrier walls and the backing element and array substrate. In certain embodiments, the second substrate such as an array is held on the interior or underside of the cover by tabs (not shown), such that when the cover is associated with the base to form a closed device, the array is contacted with the container element supported sample. Alternatively, the second substrate such as an array may be contacted with the container element supported sample by manually placing the array onto the first substrate such as a backing element before engaging the base and the cover together.

More specifically, a first substrate, e.g., a backing element, is positioned in base 34 with the one or more container elements facing out of the page, as shown in FIG. 8B shown with backing element 12 having three container elements 6 positioned in base 34. A sample S is contacted with the interiors of the container element to provide a substrate supported sample, i.e., a container element supported sample. Next, a substrate having at least one array, shown here as substrate 110 with three arrays 112, is contacted with the container element supported sample such that an enclosed assay area around each array is provided, at which point cover 32 is interlocked with base 34 in a closed configuration, with cam lever in a first or open or non-compression applying position, as shown in FIG. 8C. As mentioned above, contacting the array with the container element supported sample and interlocking the cover may be accomplished simultaneously. At this point, the cam is levered down or into the page by the actuation of cam lever 35 to a second or closed or lowered position, as shown in FIG. 8D, which causes cover 32 to apply a compression force to the container element(s).

The cam uniformly applies a compression force to compress the backing element and the array substrate together, thereby providing a compression force to the one or more container elements positioned between the backing element and the array substrate. In other words, the compression force that is applied by the subject compression device is uniformly applied to the "footprint" of the container elements. Such compression produces a substantially vapor and fluid tight seal or assay area around the one or more arrays on the array substrate.

Slide-Bridge Compression Device

FIGS. 9A-9C show an exemplary embodiment of a slide-bridge compression device according to the subject methods. As shown in the exploded view of slide-bridge device 40 in FIG. 9A, device 40 includes a cover 42, a mateable base 44 and a slide-bridge 46 that is configured to slide over cover 42 and base 44 when in a closed configuration, as shown in the assembled view of device 40 in FIG. 9C. Cover 42 is configured to uniformly spread the force applied by single knob or screw 48 of bridge 46 to the underlying structure, i.e., to the backing element/array structure or rather to the container element(s) positioned therebetween. Accordingly, slide-bridge compression device 40 is configured to apply a compression force to a backing element and an array substrate having at least one array, having at least one container element therebetween, when present in the slide-bridge device by actuating knob or screw 48 which applies a compression force to a surface of cover 42. This compression force is then uniformly spread or translated by cover 42 to the underlying backing/array substrate structure so that a uniform force is applied to the one or more container element(s) present in the device to provide a seal around the array.

Base 44 includes substrate positioning area 47 that is dimensioned to retain a substrate such as a backing element or array substrate, as shown in FIG. 9B having backing element 12 with three container elements 6 positioned in base 44. A backing element used with the device may be a separate component or may be integrally formed or molded with the base as a single piece. In use, a first substrate such as a backing element is positioned in area 47 with the one or more container elements facing the cover or forward, i.e., facing out of the page. The substrate positioning area also retains a second substrate such as an array substrate if the first substrate is a backing element, positioned in opposition to the first substrate and which is contacted with a container element supported sample positioned between the first and second substrates so that the container element(s) are closed on all sides by the fluid barrier walls and the backing element and array substrate. In certain embodiments, the second substrate such as an array is held on the interior or underside of the cover by tabs (not shown), such that when the cover is associated with the base to form a closed device, the array is contacted with the container element supported sample. Alternatively, the second substrate, e.g., an array, may be contacted with the container element supported sample by manually placing the second substrate onto the first substrate such as a backing element before engaging the base and the cover together.

As mentioned above, a feature of this device is the presence of a slide-bridge member 46 that includes a single turnable or rotatable knob or screw 48 threadably disposed within bore 49 of the bridge. In use, a first substrate, e.g., a backing element, is positioned in base 34 with the one or more container elements facing out of the page, as shown in FIG. 9B. A sample S is contacted with the interiors of the container elements to provide a substrate supported sample, i.e., a container element supported sample. Next, a second substrate having at least one array, shown here as substrate 110 with three arrays 112, is contacted with the container element supported sample such that an enclosed assay area around each array is provided, at which point cover 42 is associated with base 44 in a closed configuration. As mentioned above, contacting the array with the container element supported sample and associating the cover with the base may be accomplished simultaneously. At this point, slide bridge 46 is slideably moved over the closed housing structure and knob 48 is turned in the direction of arrows 41, as shown in FIG. 10C, which advances or threads the knob through bore 49 to contact cover 42. The knob is turned in the direction of arrows 41 an amount to apply a sufficient compression force to cover 42, which cover in turn spreads the compression force uniformly, as represented by arrows 43, to uniformly compress the backing element and the array substrate together, thereby providing a compression force to the container elements positioned between the backing element and the array substrate. In other words, the compression force that is applied by rotating the knob is uniformly applied to the "footprint" of the container elements. Such compression produces a substantially vapor and fluid tight seal or assay area around the one or more arrays on the array substrate.

Insert Bracket Compression Device

FIGS. 10A–10C show an exemplary embodiment of an insert compression device according to the subject methods. The insert bracket device is analogous to the above-described slide-bridge compression device in that a single knob or screw is employed to apply a compression force to cover 52, which is, in turn, is configured to uniformly spread the force applied by screw 48 to the underlying structure., i.e., to the backing element and array substrate or rather to the container element(s) present in the device.

As shown in the exploded view of insert bracket compression device 50 in FIG. 11A, the device includes a cover 52, a mateable base 54 and an insert bracket member 46 that is configured to drop into and slideably lock with base 54, when base 54 and cover 52 are in a closed position, as shown in the assembled view of device 50 in FIG. 10C. Cover 52 is configured to uniformly spread the force applied by knob or screw 58 to the underlying structure, i.e., to the backing element/array substrate or rather to the container element(s) positioned therebetween. Accordingly, insertable bracket compression device 50 is configured to apply a compression force to a backing element and a substrate having at least one array, and one or more container elements therebetween, when present in the insert bracket device by actuating knob or screw 58 which applies a compression force to cover 52.

This compression force is then uniformly spread or translated by cover 52 to the underlying backing/array substrate structure so that a uniform force is applied to the one or more container element(s) present in the device.

Base 54 includes substrate positioning area 57 that is dimensioned to retain a substrate such as a backing element or array, as shown in FIG. 10B having backing element 12 with three container elements 6 positioned in base 54. A backing element used with the device may be a separate component or may be integrally formed or molded with the base as a single piece. In use, a first substrate such as a backing element is positioned with the one or more container elements facing the cover or forward, i.e., facing out of the page. The substrate positioning area also retains a second substrate such as an array substrate if the first substrate is a backing element, positioned in opposition to the first substrate and which is contacted with a container element supported sample positioned between the first and second substrates so that the container element(s) are closed on all sides by the fluid barrier walls and the backing element and array substrate. In certain embodiments, the second substrate such as an array is held on the interior or underside of the cover by tabs (not shown), such that when the cover is associated with the base to form a closed device, the array is simultaneously contacted with the container element supported sample. Alternatively, the second substrate, e.g., an array, may be contacted with the container element supported sample prior to positioning the cover by manually placing the array onto the backing element before engaging the base and the cover together.

As mentioned above, a feature of this device is the presence of an insert bracket member 56 that includes a turnable or rotatable screw or knob 58 threadably disposed within bore 59 of the bracket member. In use, first substrate such as a backing element is positioned in base 54 with the one or more container elements 6 facing out of the page, as shown in FIG. 10B. A sample S is contacted with the interiors of the container elements to provide a substrate supported sample, i.e., a container element supported sample. Next, a substrate having at least one array (herein shown as substrate 110 having three arrays 112) is contacted with the container element supported sample such that an enclosed assay area around each array is provided, at which point cover 52 is associated with base 54 in a closed configuration. As mentioned above, contacting the array with the container element supported sample and associating the cover with the base may be accomplished simultaneously. At this point, insert bracket member 56 is placed onto cover 52 and slideably locked to base 54 by interlocking locking protrusions 150 on insert bracket 52 with corresponding locking recesses 152 on base 54 over the closed housing structure, as shown in FIGS. 10B and 10C. Knob 58 is turned in the manner described above for the analogous slide-bridge device. That is, turning knob 58 advances or threads the knob through bore 59 to contact cover 52. The knob is turned to apply a sufficient amount of compression force to cover 52, which in turn spreads the compression force uniformly, as described above, to uniformly compress the backing element and the array substrate together, thereby providing a compression force to the container elements positioned between the backing element and the array substrate. In other words, the compression force that is applied by rotating the knob is uniformly applied to the "footprint" of the container elements. Such compression produces a substantially vapor and fluid tight seal or assay area around the one or more arrays on the array substrate.

Multi-Point Compression Device

FIGS. 11A-11C show an exemplary embodiment of a multi-point compression device according to the subject methods. As shown in the exploded view of multi-point device 60 in FIG. 11A, the device includes a cover 62 and a mateable base 64. FIG. 11C shows the assembled device of FIG. 11A. Base 64 and cover 62 are maintained in a closed configuration by fasteners 68 that are threadably disposed in bores 69 and which engage corresponding threaded fastener holes 65 in the base, as shown in the assembled view of device 60 in FIG. 12C. The compression force that is applied by threading fasteners 68 with holes 65 is uniformly applied to the underlying structure, i.e., to the backing element/array substrate structure or rather to the container element(s) therebetween. Accordingly, multi-point compression device 60 is configured to apply a compression force to a backing element and a substrate having at least one array, and one or more container elements therebetween, when present in the multi-point device by threading fasteners 48 to holes 65 which applies a compression force to the structure retained in the device.

Base 64 includes substrate positioning area 67 that is dimensioned to retain a substrate such as a backing element or array, as shown in FIG. 11B. A backing element used with the device may be a separate component or may be integrally formed or molded with the base as a single piece. In use, a first substrate such as a backing element is positioned with the one or more container elements facing the cover or forward, i.e., facing out of the page. The substrate positioning area also retains a second substrate such as an array substrate if the first substrate is a backing element, positioned in opposition to the first substrate and which is contacted with a container element supported sample positioned between the first and second substrates so that the container element(s) are closed on all sides by the fluid barrier walls and the backing element and array substrate. In certain embodiments, the second substrate such as an array is held on the interior or underside of the cover by tabs (not shown), such that when the cover is associated with the base to form a closed device, the array is simultaneously contacted with the container element supported sample. Alternatively, the second substrate, e.g., an array, may be contacted with the container element supported sample by manually placing the array onto the backing element before engaging the base and the cover together.

As mentioned above, a feature of this device is the presence of multiple fasteners that effectively provide a uniform compression force to the structure retained in the device. In use, a first substrate such as a backing element is positioned in base 64 with the one or more container elements facing out of the page, as shown in FIG. 12B having backing element 12 with three container elements 6 positioned in base 64. A sample S is contacted with the interiors of the container elements to provide a substrate supported sample, i.e., a container element supported sample. Next, a substrate having at least one array (herein shown as substrate 110 having three arrays 112) is contacted with the container element supported sample such that an enclosed assay area around the array is provided, at which point cover 62 is associated with base 64 in a closed configuration. In this embodiment, three individual assay areas are formed around each array. As mentioned above, contacting the array with the container element supported sample and associating the cover with the base may be accomplished simultaneously. At this point, fasteners 68 are turned in the direction of arrows 61, as shown in FIG. 12C. Turning fasteners 68 advances or threads the fasteners through bores 69 to threadably engage corresponding holes 65 in base 64. The fasteners are threaded to apply a sufficient amount of compression force to compress the first and second substrates together, thereby providing a compression force to the container elements 6 positioned therebetween. In other words, the compression force that is applied by fastening the cover and the base together is uniformly applied to the "footprint" of the container elements. Such compression produces a substantially vapor and fluid tight seal or assay area around the one or more arrays on the array substrate.

Quarter-Turn Compression Device

FIG. 12 shows an exploded view of an exemplary embodiment of a quarter-turn compression device according to the subject methods. Quarter-turn compression device 70 is analogous to the multi-point compression device described above and functions in a similar fashion. However, a feature of quarter-turn device 70 is that the fasteners 78 are quarter-turn fasteners in that they only require a quarter-turn rotation to provide sufficient compression force to the structure retained between base 74 and cover 72. As such, a compression force of sufficient magnitude is applied to the first and second substrates with minimal effort on the part of the user.

Substrate Receiving Frame

Also provided by the subject invention are substrate receiving frames for positioning a substrate 110 having at least one array therein before being positioned in a compression device. In other words, the frames are dimensioned to be used with the subject compression devices. FIG. 12 shows an exemplary embodiment of a substrate receiving frame 8 having substrate 110 positioned therein. Substrate receiving frame 8 has an opening 17 for positioning the substrate 110 therein using any suitable mechanical, physical or chemical means. Usually, the frame will include ledges or rails (not shown) onto which the substrate 110 is positioned. The substrate receiving frame 8 may be compatible with an array reader such as a MICROARRAY scanner available from Agilent Technologies of Palo Alto, Calif, where such a compatible array reader will typically have a suitable mounting means for receiving and releasably retaining the substrate receiving frame 8 in a known position. Accordingly, after the array assay is complete, the frame 8 with the substrate 110 therein may be directly placed, i.e., mounted, into an array reader. That is, the substrate receiving frame 8 may be used as a means to handle a substrate 110 both during the assay and the reading of the array. In certain embodiments, the array is provided to the user pre-assembled or pre-packaged in a receiving frame, which may be pre-assembled or pre-packaged in a subject compression device.

The size and shape of a substrate receiving frame 8 may vary according to the size and shape of the substrate 110 and corresponding compression device employed to perform an array assay. By way of example only and not limitation, in certain embodiments the substrate receiving frame 8 is rectangular in shape and the length thereof typically ranges from about 10 mm to about 200 mm, usually from about 20 mm to about 100 mm and more usually from about 22 mm to about 80 mm, the width typically ranges from about 10 mm to about 200 mm, usually from about 20 mm to about 100 mm and more usually from about 22 mm to about 50 mm and the thickness typically ranges from about 1 mm to about 100 mm, usually from about 3 mm to about 50 mm and more usually from about 5 mm to about 20 mm.

The subject substrate receiving frames 8 may be manufactured from a variety of materials, with the only limitation being that the such materials used to fabricate the subject frames will not substantially interfere with the assay reagents and assay and will have minimal non specific binding characteristics, e.g., substantially chemically inert, thermally stable, etc. Specifically, the materials should be chemically and physically stable under conditions employed for array assay procedures. Examples of such materials may include, but are not limited to, plastics such as polytetrafluoroethylene, polypropylene, polystyrene, polycarbonate, PVC, and blends thereof, stainless steel and alloys thereof, siliceous materials, e.g., glasses, fused silica, ceramics and the like. In those embodiments where the substrate receiving frame 8 is also compatible and thus used with an array reader or scanner, the material used will be compatible with the reader as well. For example, where the reader is an optical scanner, the material of the substrate receiving frame 8 will usually be opaque, such as an opaque plastic, e.g., black acrylonitrile-butadiene-styrene (ABS) plastic (although other material could be used as well).

Array Holders

Also provided by the subject invention are array holders suitable for use with the subject compression devices. In other words, the array holders are dimensioned to be used with the subject compression devices. More specifically, the subject array holders are used to retain the substrates which include one or more arrays. The array holders of the subject invention are configured to be used with the subject compression devices described above and may also be used with the subject substrate receiving frames described above. The array holders of the subject invention may be configured to be compatible with array scanners or readers for interrogating or reading the array after an assay has been performed such as a hybridization assay or the like, e.g., array optical scanners such as the MICROARRAY scanner available from Agilent Technologies, Inc. of Palo Alto, Calif., where such a compatible scanner will typically have a suitable mounting means for receiving and releasably retaining the array holder in a known position. In certain embodiments, the array is provided to the user pre-assembled or pre-packaged in an array holder, which may be pre-assembled or pre-packaged in a subject receiving frame and/or subject compression device.

The subject array holders serve multiple purposes such as substrate edge protection, compatibility with array scanners and the ability to grasp and manipulate an array without contacting the array itself, e.g., during a wash protocol, during transport, e.g., to an array reader, and the like. Furthermore, the array holders enable a wide range of substrate sizes to be used with the subject array hybridization chambers. That is, a substrate shorter in length than a typical substrate, e.g., shorter in length than a typical 1" by 3" microscope slide in certain instances, may be first retained in the array holder which itself is about 1" by about 3", or is the size of a typical substrate or of a suitable size that is compatible with the array assay device or frame. Thus, when a substrate having a length shorter than it able to be accommodated by a subject array assay device or receiving frame, for example shorter in length than about 3" is retained by a subject holder, the shorter substrate may still be used with a subject compression device. In certain embodiments, spacers may be added to the holder as well to accommodate the remaining volume/area remaining from the shorter length substrate to allow an appropriate seal to be produced by a container element and the volume within the assay area(s) to remain constant no matter the dimensions of the substrate.

FIG. 13 shows an exemplary embodiment of a subject array holder. Array holder 200 includes two opposed side portions 204a and 204b with a channel 206 positioned therebetween, and extending in a direction between open end 202a and closed end 202b. Opposed side portions 204a and 204b have ledges 204 running the lengths of side portions 204a and 204b which receive and retain a substrate, i.e. upon which a substrate rests. In use, a substrate is inserted into holder 200 via open end 202a. FIG. 14 shows holder 200 having a substrate 300 having one or more arrays 302 retained therein and a substrate 310 having one or more arrays 312 partially inserted through open end 202a. As is shown, substrates 300 and 310 have lengths shorter than the length of the holder 200, e.g., may be shorter than required for use with a subject compression device and/or substrate receiving frame and thus spacers 305 are used to take-up the remaining space.

The size and shape of an array holder 200 may vary according to the size and shape of a substrate and corresponding compression device. By way of example only and not limitation, in certain embodiments the array holder 200 is rectangular in shape and the length thereof typically ranges from about 10 mm to about 200 mm, usually from about 20 mm to about 100 mm and more usually from about 22 mm to about 80 mm, the width typically ranges from about 10 mm to about 100 mm, usually from about 20 mm to about 50 mm and more usually from about 22 mm to about 30 mm and the thickness typically ranges from about 1 mm to about 100 mm, usually from about 3 mm to about 50 mm and more usually from about 5 mm to about 20 mm.

The subject holders may be manufactured from a variety of materials, with the only limitation being that the such materials used to fabricate the subject holders will not substantially interfere with the assay reagents and assay and will have minimal non specific binding characteristics, e.g., substantially chemically inert, thermally stable, etc. Specifically, the materials should be chemically and physically stable under conditions employed for array assay procedures. Examples of such materials may include, but are not limited to, plastics such as polytetrafluoroethylene, polypropylene, polystyrene, polycarbonate, PVC, and blends thereof, stainless steel and alloys thereof, siliceous materials, e.g., glasses, fused silica, ceramics and the like. In those embodiments where the array holder 200 is also compatible and thus used with an array reader or scanner, the material used will be compatible with the reader as well For example, where the reader is an optical scanner, the material of the array holder will usually be opaque, such as an opaque plastic, e.g., black acrylonitrile-butadiene-styrene (ABS) plastic (although other material could be used as well).

Systems

Also provided by the subject invention are systems that include the subject compression devices. The subject systems include a subject compression device, an array substrate having at least one array, a backing element, and at least one container element, as described above. In certain embodiments, the subject systems may further include reagents employed in array based assay protocols, including sample preparation reagents, e.g., labeling reagents, etc; washing fluids; etc.

Methods

As summarized above, methods are provided for performing an array-based assay such as a hybridization assay or any other analogous binding interaction assay. A feature of the present methods is that a sample suspected of including an analyte of interest, e.g., a target molecule, is first contacted with a first surface of a first substrate, e.g., a first surface of a backing element or an array, to produce a substrate supported sample, e.g., a backing element-supported sample, where the first surface is bounded on all sides to define a container element which retains the sample. Once a substrate supported sample is provided, a second substrate n array is contacted to the supported sample, a compression force is applied to hold the backing element and the array substrate together in a fixed position and the remainder of the assay is carried out. As such, the subject methods are characterized by having an initial step in which a substrate supported sample, e.g., backing element supported, is produced from an initial sample, where the substrate supported sample is then contacted with a second substrate such as an array and a compression force is applied to the first and second substrates to provide a seal around the array. Accordingly, the subject methods differ significantly from prior art protocols at least in that sample may be directly contacted with a container element to provide a substrate supported sample using a pipette or the like and, as such, does not require a needle, where prior art methods often include a first step of assembling a closed chamber around an array/gasket configuration having normally closed ports, where resilient, self-sealing gasket portions provide closure to the access ports. Accordingly, such prior art protocols then require a step of introducing sample to the array by penetrating the closed chamber through the normally closed gasket portions, where such penetration requires a hollow needle or other sharp-tipped sample introduction element.

Thus, the resultant substrate supported sample is contacted with a second substrate and a compression force is applied to the first and second substrates (i.e., to the backing element and the array) to compress them together. In this manner, the sample is effectively retained within the container element(s) to prevent sample leakage and/or evaporation from the assay area and all parts of the array are contacted by sample with uniformly distributed reactants, i.e., all parts of the array are bathed in the same concentrations of reactants during the array assay.

Accordingly, the subject methods include contacting a sample, or other fluid such as wash buffer, etc., with a first surface of a first substrate, i.e., a first surface of a backing element. A feature of the first surface of the first substrate is that it is bounded on all sides by a fluid barrier to define a container element. That is, a sealing element is positioned on a first surface of a first substrate to provide a fluid barrier that is enclosed on all sides so that a sample may be deposited and retained by the barrier. The fluid barrier may be an integrally formed fluid barrier with respect to the first substrate, or may be a separate component that is otherwise adhered to the first substrate. Stull further, the fluid barrier may be a removable fluid barrier. The fluid barrier may be positioned on the backing element or on the array substrate, whichever is convenient for a given protocol. In further describing the subject methods, reference to a backing element having a container element will be primarily used to describe the invention, where such description is exemplary only and is in no way intended to limit the scope of the invention.

Figure 1:
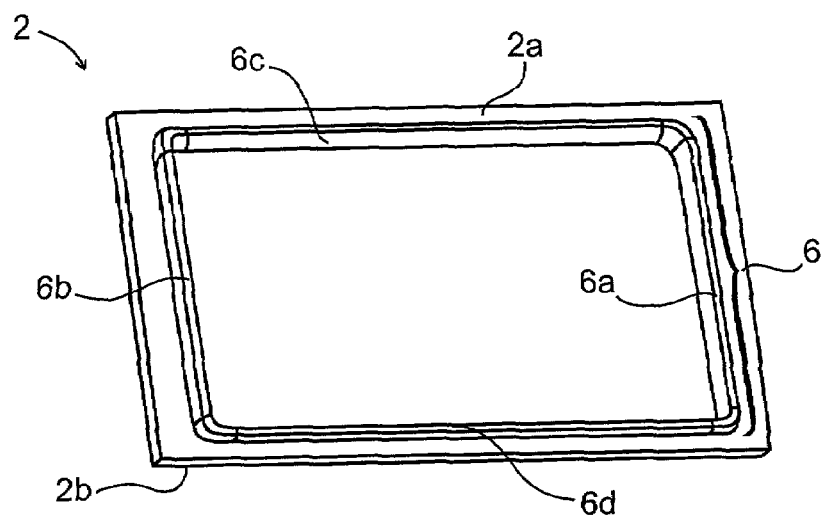
FIG. 1 shows an exemplary embodiment of a subject backing element having a single container element.
Figure 2:
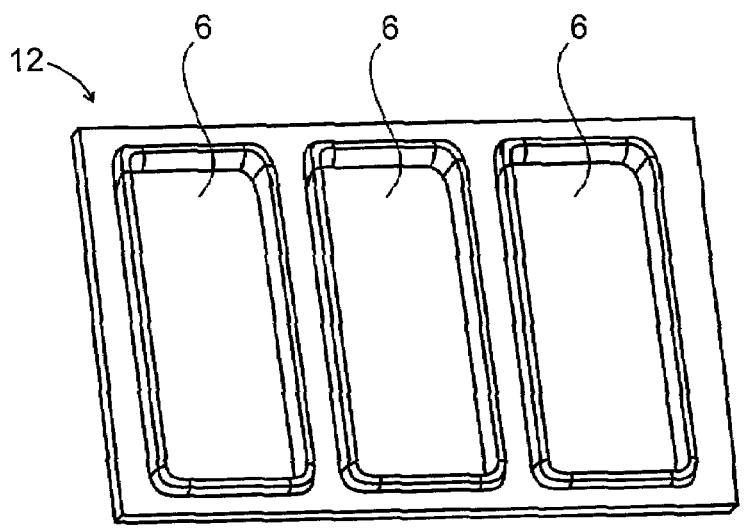
FIG. 2 shows an exemplary embodiment of a subject backing element having multiple container elements.
Figure 3:
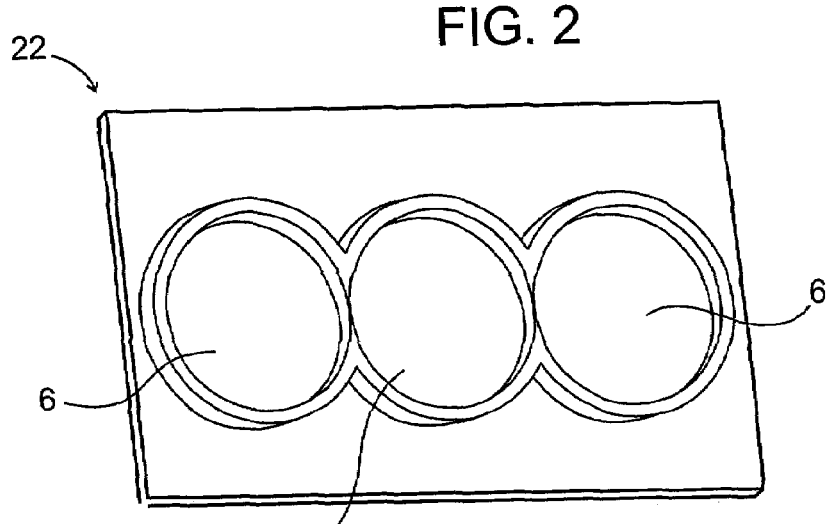
FIG. 3 shows another exemplary embodiment of a subject backing element having multiple container elements.

FIGS. 1-3 illustrate various exemplary embodiments of a subject substrate that is bounded on all sides by a fluid barrier, where analogous structures suitable for use with the present invention are also described in copending U.S. provisional application Ser. No. 10/461,826, entitled "Methods of Performing Array Based Assays and Compositions For Practicing the Same", filed on Jun. 14, 2002; and U.S. application Ser. No. 10/172,850, entitled "Form in Place Gaskets for Assays", filed on Jun. 14, 2002, the disclosures of which are herein incorporated by reference.

Turning to FIG. 1, backing element 2, to which the fluid sample may be initially contacted to produce the substrate supported sample is a substrate or solid support that generally includes a first planar surface 2a opposite second surface 2b, where first surface 2a may be regular or have irregularities. Substrate 2 may be fabricated from a single material, or be a composite of two or more different materials. While the nature of this substrate may vary considerably, representative materials from which it may be selected include, but are not limited to: plastics, such as polyacrylamide, polyacrylate, polymethacrylate, polyesters, polyolefins, polyethylene, polytetrafluoro-ethylene, polypropylene, poly (4-methylbutene), polystyrene, poly(ethylene terephthalate); fused silica (e.g., glass); bioglass; silicon chips, ceramics; metals; and the like, where in certain embodiments optically transparent substrate are employed. In many embodiments, the backing element is made from glass.

As shown, backing element includes a separator such that it is bounded on all sides by a fluid barrier to form a container element for containing fluid. As mentioned above, in certain embodiments the array substrate includes the fluid barrier or the fluid barrier may be a separate component. The fluid barrier will be primarily further described as positioned on a backing element, where such description is for exemplary purposes only and is in no way intended to limit the scope of the invention. In any case, the separator or fluid barrier of the subject invention may be at least one wall surrounding a first surface 2a in a manner sufficient to form container element 6 defined by the barrier and first surface 2a, where the number of distinct walls surrounding first surface 2a will depend on the cross-sectional shape of the container element, e.g., 1 wall for a container having a circular cross-sectional shape and 4 walls for a container having a square cross-sectional shape. As shown in FIG. 1, container element in this embodiment has walls 6a, 6b, 6c and 6d. The container element may have a variety of cross-sectional shapes, including circular, triangular, rectangular, square, pentagon, hexagon, etc., including irregular, but will usually have a rectangular, circular or square cross-sectional shape. Therefore, the number of distinct walls surrounding first surface 2a of first substrate 2 will be at least one, and may be 2, 3, 4, 5, 6 or more, depending on the cross-sectional shape.

The height or thickness of the container elements may vary, where the height is generally at least about 5-10 micrometers, usually at least about 15 micrometers and more usually at least about 20 micrometers, where in many embodiments the height may be about 25 micrometers to about 100 micrometers or even up to about 250 micrometers or more, where the height may be up to about 500 micrometers, even up to about 1000 micrometers or up to about 5000 micrometers or more, where the height may be a few millimeters or more in certain embodiments.

The width of a container element, defined by the distance from one side of a container element through the wall to the opposing side of the container element, may vary, where the width is generally at least about 20-50 micrometers to about 150 micrometers, may be at least about 150 micrometers to about 250 micrometers, sometimes up to about 300 micrometers, or up to about 400 micrometers, or even up to about 500 micrometers in certain embodiments, even up to about 700 micrometers or even up to about 1000 micrometers or more in some embodiments. For example, the width may range up to about 1.5 mm, sometimes up to about 3 mm, and sometimes up to about 6 mm.

The fluid barriers or walls may be fabricated from the same material as tho substrate upon which it is positioned, e.g., a backing element, or a different material from the substrate upon which it is positioned. In yet other embodiments, the barriers are hydrophobic strips, e.g., made hydrophobic by thc presence of a hydrophobic film or coating of a hydrophobic material, or analogous structures serve as the container described above. For an example of such embodiments, see Col. 11, line 42 through Col. 12, line 67 of U.S. Pat. No. 5,807,522, the disclosure of which is herein incorporated by reference, The fluid barrier may be a form-in-place gasket as described in U.S. application Ser. No. 10/172,850, entitled "Form in Place Gaskets for Assays", filed on Jun. 14, 2002, incorporated herein by reference as mentioned above. As recited in the Ser. No. 10/172,850 application, a form-in-place gasket, as the term is used herein, refers to a gasket which is formed on a gasket surface in a process that involves depositing a gasket material onto the gasket surface. The term "form-in-place gasket" also encompasses a plurality of discontinuous portions of gasket disposed on a surface, such as when farmed by depositing gasket material on the surface discontinuously and then curing the gasket material. The gasket surface is the surface upon which the gasket is formed (or is intended to be formed). The mating surface is the surface that is complementary to the gasket surface and is disposed against the gasket formed on the gasket surface (or is intended to be disposed against the gasket formed on the gasket surface). Gasket material references a fluid material having properties that render the fluid material suitable for formation of a gasket. As used below, "gasket" typically references a form-in-place gasket according to the present invention, unless the context clearly indicates otherwise. "Fluid tight" when used to describe a seal, a chamber, or other feature references an ability to resist flow of a fluid past an intended boundary (typically defined by a gasket), but yet permits fluid flow within intended boundaries, such as on one side of a seal, into or out of a chamber via a port, or along the length of a channel. "Mixing feature" references structures formed on a surface (e.g. by depositing gasket material on the surface) that, due to the geometry or physical configuration of the structure, serves to aid mixing of the contents of a chamber. In certain embodiment, a "substrate" may include materials that are homogenous, heterogenous, or otherwise, and may include individual component parts that are combined to produce the substrate. Similarly, in certain embodiments, a "cover" may include materials that are homogenous, heterogenous, or otherwise, and may include individual component parts that are combined to produce the cover. "Substantially defined", as it relates to a substrate, a cover, and gasket "sulbstantially defining" an assay chamber, means that the chamber need not be totally enclosed (e.g. the chamber may have one or more ports, or orifices), and/or that other elements (other than the substrate, cover, and gasket) may define a portion (e.g. less than about 20% of the surface area defining the assay chamber) of the assay chamber or may contribute (e.g. up to about 20% of the surface area defining the assay chamber) to defining the assay chamber. "Substantially" in other contexts means generally at least about 80% of the property or state referred to, unless the context clearly dictates othewise. "Pliable" references a property of a material which is pliant or compressible. "Self-leveling" references a property of a material which tends to have a certain given thickness under a given set of conditions, and in particular references the property of certain gasket materials to flow, or to "slump", (after being deposited on a gasket surface but prior to completion of curing to a certain thickness, where the thickness depends on properties of the gasket material applied and the conditions of application, including the conditions used for curing the gasket material and the properties of the surface on which the gasket material is deposited. "Non-slumping" references a property of a material which does not flow, or which maintains an essentially constant conformation, after being deposited on a gasket surface but prior to completion of curing. Of course, non-slumping materials may be manipulated to result in a chanced conformation after begining deposited on a gasket surface but prior to completion of curing, e.g. by being squeezed between a substrate and a cover, and this does not alter their "non-slumping" property. "Uniform thickness" describes gaskets or gasket materials applied to a surface such that substantially the entire gasket or applied gasket material has a given thickness (plus or minus about 20%), wherein, the thickness of the gasket measured at various points varies by less than 20% of the given thickness of the gasket.

The container element generally has a volume, defined by the surface of the substrate on which it is positioned and the fluid barrier walls, of at least about 1-5 μl, where the volume may range from about 1 μl to about 1000 μl, usually from about 10 μl to about 1000 μl, where the volume may be as great as about 1000 μl to about 5000 μl or greater.

In certain embodiments, more than one container element is present, where the various container elements may be formed from one or more contiguous fluid barriers or may be formed from separate fluid barriers. The multiple container elements may be used with a substrate having more than one array, where some or all of the arrays may be the same or some or all may be different, to provide separate or individual container elements around each array such that multiple samples may be tested with multiple arrays without cross-contamination. FIG. 2 shows an exemplary embodiment of backing element 12 having three rectangular container elements 6 positioned thereon and FIG. 3 shows an exemplary embodiment of backing element 22 have three circular container elements 6 formed from a contiguous fluid barrier. The number of container elements shown is exemplary only and may vary depending on a variety of factors such as the number of arrays, the dimensions of the substrates, etc. Typically, the number of container elements ranges from about 1 to about 100, but may include greater than about 100 container elements in certain embodiments, where the number may be as great as about 100 container elements or even as great as about 500 container elements or more in some embodiments.

As described, a backing element is dimensioned to fit with an array (a substrate having at least one array thereon) to produce an array assay area around the array having an array assay volume that is bounded on the top and bottom by the array substrate surface and a surface of the backing element, respectively, and on the sides by the fluid barrier walls of the container element.

In practicing the subject methods, a quantity of a fluid sample to be assayed is first contacted with the first surface of a first substrate, further described with reference to a first surface of a backing element, to produce a substrate support sample. That is, the sample is introduced into the container element present on the first surface of a first substrate, e.g., a backing element, so that the sample is retained thereby. In those embodiments having more than one container element, the same sample may be applied to one or more container element, for example when it is desirable to test the same sample with different arrays during the same assay procedure, or a different sample may be applied to one or more containers than is applied to one or more other containers, for example when it is desirable to test different samples with the same array during the same array assay procedure. The sample may be introduced into a container element using any convenient protocol, where in many embodiments a deposition type protocol is employed, e.g., by pipette or the like. As mentioned above, an important feature of the subject methods is that a needle is not required to apply the sample to the container element because the container element is easily accessible at its opened top end at this point in the subject methods.

Once the sample has been contacted with the first surface of the first substrate and the sample is contained by the container element, the resultant substrate supported sample, e.g., backing element or container supported sample, is then contacted with a second substrate (an array of binding agents that include a binding agent specific for the analyte of interest if the first substrate is a backing element) and a compression force is applied to the structure of the backing element/array to provide a fluid tight seal around the array. That is, at any point, the first and second substrates are operatively positioned in a compression device such as a compression device described above. For example, the first substrate may be positioned in a compression device (e.g., the first substrate may be provided to the user already in a compression device for example integrally formed therein, etc.), a sample applied to the first substrate in the compression device and then the second substrate may be positioned thereover. In another example, the first substrate may be initially outside the compression device, sample contacted thereto, the second substrate positioned thereover and the resultant structure then positioned in a compression device. In any case, the sample is contacted with the array, a compression force is applied to the backing element/array structure to retain the sample in contact with the array, where the sample is contacted with the array under conditions sufficient for the analyte to bind to its respective binding pair member that is present on the array. Thus, if the analyte of interest is present in the sample, it binds to the array at the site of its complementary binding member and a complex is formed on the array surface. Depending on the nature of the analyte(s), the array may vary greatly. Representative arrays are now reviewed in greater detail.

The arrays employed in the subject methods are typically biopolymeric arrays. These biopolymeric arrays include a plurality of ligands or molecules or probes (i.e., binding agents or members of a binding pair) deposited onto the surface of a substrate in the form of an "array" or pattern. These biopolymeric arrays include at least two distinct polymers that differ by monomeric sequence attached to different and known locations on the substrate surface. Each distinct polymeric sequence of the array is typically present as a composition of multiple copies of the polymer on a substrate surface, e.g., as a spot or feature on the surface of the substrate. The number of distinct polymeric sequences, and hence spots or similar structures, present on the array may vary, where a typical array may contain more than about ten, more than about one hundred, more than about one thousand, more than about ten thousand or even more than about one hundred thousand features in an area of less than about 20 cm$^2$ or even less than about 10 cm$^2$. For example, features may have widths (that is, diameter, for a round spot) in the range from about 10 µm to about 1.0 cm. In other embodiments, each feature may have a width in the range from about 1.0 µm to about 1.0 mm, usually from about 5.0 µm to about 500 µm and more usually from about 10 µm to about 200 µm. Non-round features may have area ranges equivalent to that of circular features with the foregoing width (diameter) ranges. At least some, or all, of the features are of different compositions (for example, when any repeats of each feature composition are excluded, the remaining features may account for at least about 5%, 10% or 20% of the total number of features). Interfeature areas will typically (but not essentially) be present which do not carry any polynucleotide (or other biopolymer or chemical moiety of a type of which the features are composed). Such interfeature areas typically will be present where the arrays are formed by processes involving drop deposition of reagents, but may not be present when, for example, photolithographic array fabrication process are used. It will be appreciated though, that the interfeature areas, when present, could be of various sizes and configurations. The spots or features of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like.

In the broadest sense, the arrays are arrays of polymeric or biopolymeric ligands or molecules, i.e., binding agents, where the polymeric binding agents may be any of: peptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like.

The arrays may be produced using any convenient protocol. Various methods for forming arrays from pre-formed probes, or methods for generating the array using synthesis techniques to produce the probes in situ, are generally known in the art. See, for example, Southern, U.S. Pat. No. 5,700,637; Pirrung, et al., U.S. Pat. No. 5,143,854 and Fodor, et al. (1991) *Science* 251:767-777, the disclosures of which are incorporated herein by reference and PCT International Publication No. WO 92/10092. For example, probes can either be synthesized directly on the solid support or substrate to be used in the array assay or attached to the substrate after they are made. Arrays may be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos.: 6,242,266, 6,232,072, 6,180,351, 6,171,797, 6,323,043; and U.S. patent application Ser. No. 09/302,898 filed Apr. 30, 1999 by Caren et al., and the references cited therein, the disclosures of which are herein incorporated by reference. Other drop deposition methods may be used for fabrication. Also, instead of drop deposition methods, photolithographic array fabrication methods may be used such as described in U.S. Pat. Nos. 5,599,695, 5,753,788, and 6,329,143, the disclosures of which are herein incorporated by reference. As mentioned above, interfeature areas need not be present, particularly when the arrays are made by photolithographic methods as described in those patents.

A variety of solid supports or substrates may be used, upon which an array may be positioned. In certain embodiments, a plurality of arrays may be stably associated with one substrate. For example, a plurality of arrays may be stably associated with one substrate, where the arrays are spatially separated from some or all of the other arrays associated with the substrate.

The substrate may be selected from a wide variety of materials including, but not limited to, natural polymeric materials, particularly cellulosic materials and materials derived from cellulose, such as fiber containing papers, e.g., filter paper, chromatographic paper, etc., synthetic or modified naturally occurring polymers, such as nitrocellulose, cellulose acetate, poly (vinyl chloride), polyamides, polyacrylamide, polyacrylate, polymethacrylate, polyesters, polyolefins, polyethylene, polytetrafluoro-ethylene, polypropylene, poly (4-methylbutene), polystyrene, poly (ethylene terephthalate), nylon, poly(vinyl butyrate), cross linked dextran, agarose, etc.; either used by themselves or in conjunction with other materials; fused silica (e.g., glass), bioglass, silicon chips, ceramics, metals, and the like. For example, substrates may include polystyrene, to which short oligophosphodiesters, e.g., oligonucleotides ranging from about 5 to about 50 nucleotides in length, may readily be covalently attached (Letsinger et al. (1975) *Nucl. Acids Res.* 2:773-786), as well as polyacrylamide (Gait et al. (1982) *Nucl. Acids Res.* 10:6243-6254), silica (Caruthers et al. (1980) *Tetrahedron Letters* 21:719-722), and controlled-pore glass (Sproat et al. (1983) *Tetrahedron Letters* 24:5771-5774). Additionally, the substrate can be hydrophilic or capable of being rendered hydrophilic.

Suitable substrates may exist, for example, as sheets, tubing, spheres, containers, pads, slices, films, plates, slides, strips, disks, etc. The substrate is usually flat, but may take on alternative surface configurations. The substrate can be a flat glass substrate, such as a conventional microscope glass slide, a cover slip and the like. Common substrates used for the arrays of probes are surface-derivatized glass or silica, or polymer membrane surfaces, as described in Maskos, U. et al., *Nucleic Acids Res*, 1992, 20:1679-84 and Southern, E. M. et al., *Nucleic acids Res*, 1994, 22:1368-73.

Each array may cover an area of less than about 100 cm$^2$, or even less than about 50 cm$^2$, 10 cm$^2$ or 1 cm$^2$. In many embodiments, the substrate carrying the one or more arrays will be shaped generally as a rectangular solid (although other shapes are possible), having a length of more than about 4 mm and less than about 1 m, usually more than about 4 mm and less than about 600 mm, more usually less than about 400 mm; a width of more than about 4 mm and less than about 1 m, usually less than about 500 mm and more usually less than about 400 mm; and a thickness of more than about 0.01 mm and less than about 5.0 mm, usually more than about 0.1 mm and less than about 2 mm and more usually more than about 0.2 and less than about 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least about 20%, or about 50% (or even at least about 70%, 90%, or 95%), of the illuminating light incident on the substrate as may be measured across the entire integrated spectrum of such illuminating light or alternatively at 532 nm or 633 nm.

Immobilization of the probe to a suitable substrate may be performed using conventional techniques. See, e.g., Letsinger et al. (1975) *Nucl. Acids Res.* 2:773-786; Pease, A. C. et al., *Proc. Nat. Acad. Sci. USA*, 1994, 91:5022-5026, and "Oligonucleotide Synthesis, a Practical Approach," Gait, M. J. (ed.), Oxford, England: IRL Press (1984). The surface of a substrate may be treated with an organosilane coupling agent to functionalize the surface. See, e.g., Arkins, "Silane Coupling Agent Chemistry," *Petrarch Systems Register and Review*, Eds. Anderson et al. (1987) and U.S. Pat. No. 6,258,454.

Referring first to FIG. 4, typically biopolymeric arrays of the present invention use a contiguous planar substrate 110 carrying an array 112 disposed on a rear surface 111*b* of substrate 110. It will be appreciated though, that more than one array (any of which are the same or different) may be present on rear surface 111*b*, with or without spacing between such arrays. That is, any given substrate may carry one, two, four or more arrays disposed on a front surface of the substrate and depending on the use of the array, any or all of the arrays may be the same or different from one another and each may contain multiple spots or features. The one or more arrays 112 usually cover only a portion of the rear surface 111*b*, with regions of the rear surface 111*b* adjacent the opposed sides 113*c*, 113*d* and leading end 113*a* and trailing end 113*b* of slide 110, not being covered by any array 112. A front surface 111*a* of the slide 110 does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features of biopolymers, e.g., in the form of polynucleotides. All of the features may be different, or some or all could be the same. Interfeature areas, if present, could be of various sizes and configurations. Each feature carries a predetermined biopolymer such as a predetermined polynucleotide (which includes the possibility of mixtures of polynucleotides). It will be understood that there may be a linker molecule (not shown) of any known types between the rear surface 111*b* and the first nucleotide.

Substrate 110 may carry on front surface 111*a*, an identification code (not shown), e.g., in the form of bar code or the like printed on a substrate in the form of a paper label attached by adhesive or any convenient means. The identification code contains information relating to array 112, where such information may include, but is not limited to, an identification of array 112, i.e., layout information relating to the array(s), etc.

To contact the substrate supported sample with the second substrate, the first and second substrates, (i.e., the backing element and array, with one or more container elements having sample therein positioned between the two) are brought together in a manner sufficient so that the sample contacts the ligands of the array and a compression force is applied to provide a fluid impermeable seal around the array to retain the sample in the array assay area. In other words, the sample is contained in the container element(s) and is sandwiched between the backing element and the array so as to be confined to a fixed area, and maintained therein by the application of compression force. FIG. 5 shows a cross-sectional view of a backing element 2 having container element 6 (herein represented by walls 6*c*, and 6*d*) wherein array 112 is contacted with the substrate supported sample S (represented herein as stippling).

As described above, a feature of the subject methods is that, once the substrate supported sample is contacted with a second substrate, a compression force is applied to the resultant structure, i.e., the substrate carrying the array and the backing element, to compress or press the backing element and the substrate of the array together with the container supported sample therebetween. As such, the application of this compression force ensures that the array and backing element remain positioned relative to each other in such a way as to provide a substantially vapor and fluid tight seal or barrier around the array defined by the walls of the fluid barrier of the container element, the first surface of the backing element and the array substrate. The compression force is applied uniformly to the backing element/array structure and thus uniformly to the fluid barrier therebetween so as to prevent leakage and/or evaporation of the sample from the enclosed area. This compression force may be applied using any convenient method, e.g., manually, or with the aid of a compression device configured to provide a suitable compression force to the backing element and the substrate carrying the array. The compression device used to apply the compression force may be a slideably engageable compression device, a cam compression device, a slide-bridge compression device, an insert bracket compression device, a multi-point compression device and a quarter-turn compression device, as described above. Such compression devices enable the application of a uniform compression force to the walls of the container element to prevent leakage and/or evaporation of sample therefrom.

The compression force may be applied, for example by a compression device such as a subject compression device, to opposing surfaces of the backing element and the array substrate, or may be applied, to one of the surfaces, e.g., applied solely to a surface of the array substrate, which in turn applies a compression force to the backing element, or vice versa. In either case, the backing element and the array substrate are compressed together by the application of a compression force.

While maintaining the backing element and array in a compressed state, the resultant compressed sample contacted array structure is then maintained under conditions sufficient, and for a sufficient period of time, for any binding complexes between members of specific binding pairs to occur. Where desired, the sample may be agitated to ensure contact of the sample with the array. In the case of hybridization assays, the substrate supported sample is contacted with the array under stringent hybridization conditions, whereby complexes are formed between target nucleic acids that are complementary to probe sequences attached to the array surface, i.e., duplex nucleic acids are formed on the surface of the substrate by the interaction of the probe nucleic acid and its complement target nucleic acid present in the sample. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, followed by washing the filters in 0.1×SSC at about 65° C. Hybridization involving nucleic acids generally takes from about 30 minutes to about 24 hours, but may vary as required. Stringent hybridization conditions are hybridization conditions that are at least as stringent as the above representative conditions, where conditions are considered to be at least as stringent if they are at least about 80% as stringent, typically at least about 90% as stringent as the above specific stringent conditions. Other stringent hybridization conditions are known in the art and may also be employed, as appropriate.

Once the incubation step is complete, the array is typically washed at least one time to remove any unbound and non-specifically bound sample from the substrate, generally at least two wash cycles are used. As such, the compression force is relieved to provide access to the array and the array is contacted with one or more washing agents, where the array may be washed while positioned in a compression device, if used, or may be removed from a compression device to be washed. If a substrate receiving frame and/or array holder is used, as will be described below, the array may remain retained thereby or removed from the substrate receiving frame and/or array holder during washing. Washing agents used in array assays are known in the art and, of course, may vary depending on the particular binding pair used in the particular assay. For example, in those embodiments employing nucleic acid hybridization, washing agents of interest include, but are not limited to, salt solutions such as sodium, sodium phosphate and sodium, sodium chloride and the like as is known in the art, at different concentrations and may include some surfactant as well.

Following the washing procedure, as described above, the array is then interrogated or read so that the presence of any resultant binding complexes on the array surface are detected, e.g., through use of a signal production system, e.g. an isotopic or fluorescent label present on the analyte, etc. The presence of the analyte in the sample is then deduced from the detection of binding complexes on the substrate surface.

The above-described methods find use in a variety of different applications, where such applications are generally analyte detection applications in which the presence of a particular analyte in a given sample is detected at least qualitatively, if not quantitatively.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g. a member of signal producing system. Following sample preparation, the sample is first contacted with the first surface of the first substrate to produce a substrate supported sample, as described above, which product is then contacted with the array, a compression force is applied to the resultant structure and the hybridization is performed under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. Patents describing methods of using arrays in various applications include U.S. Pat. Nos.: 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference.

Where the arrays are arrays of polypeptide binding agents, e.g., protein arrays, specific applications of interest include analyte detection/proteomics applications, including those described in U.S. Pat. Nos.: 4,591,570; 5,171,695; 5,436,170; 5,486,452; 5,532,128; and 6,197,599; as well as published PCT application Nos. WO 99/39210; WO 00/04832; WO 00/04389; WO 00/04390; WO 00/54046; WO 00/63701; WO 01/14425; and WO 01/40803; the disclosures of the United States priority documents of which are herein incorporated by reference.

The subject methods also include retaining a substrate having at least one array in a substrate receiving frame and/or an array holder, positioning the at least one array retained in the frame and/or holder in a compression device having a backing element, forming a fluid barrier to provide one or more container elements round the array(s), applying a compression force to the backing element and array substrate, e.g., on opposing surfaces of the backing element and array substrate, to compress them together and performing an array assay with the at least one array in the frame and/or holder. Following the completion of the array assay, the compression force is relieved and the frame and/or the holder with the substrate having at least one array retained thereby is removed from the compression device and directly placed, i.e., operatively mounted, into or on an array scanner or reader. In this manner, the at least one array may then be read or scanned by the array reader while the array is still held by the substrate receiving frame and/or array holder. That is, the substrate receiving frame and/or array holder may be used to handle an array both during the assay and during the scanning or reading of the array. The above described general methods for positioning and retaining a substrate having at least one array in a substrate receiving frame and/or an array holder, placing the retained substrate having at least one array in a compression device, performing an array assay using the compression device and retained substrate, removing the retained substrate having at least one array from the compression device and mounting the retained substrate, i.e., the substrate held by the receiving frame and/or array holder, in or on an array scanner and scanning the at least one array while the array is retained by the substrate receiving frame and/or the array holder may be employed with the array assay compression devices described herein or any analogous compression device.

Reading of the array may be accomplished by illuminating the array and reading the location and intensity of resulting fluorescence at each feature of the array to detect any binding complexes on the surface of the array. For example, a scanner may be used for this purpose that is similar to the AGILENT MICROARRAY SCANNER available from Agilent Technologies, Palo Alto, Calif. Other suitable apparatus and methods are described in U.S. patent applications: Ser. No. 09/846125 "Reading Multi-Featured Arrays" by Dorsel et al.; and Ser. No. 09/430214 "Interrogating Multi-Featured Arrays" by Dorsel et al.; which references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing), as now described in greater detail.

The subject methods may also include pre-assembling or pre-packaging, i.e., pre-loading, a substrate having at least one array in a compression device at a first site, e.g., a manufacturing facility or the like, and transporting the pre-packaged array for use in an array assay to a remote or second site. By "second site" in this context is meant a site other than the site at which the backing element is pre-packaged in compression device. For example, a second site could be another site (e.g., another office, lab, etc.) in the same building, city, another location in a different city, another location in a different state, another location in a different country, etc. Usually, though not always, the first site and the second site are at least in different buildings, and may be at least one mile, ten miles, or at least one hundred miles apart. "Transporting" in this context refers to any means of getting the pre-packaged backing element from one site to the next, i.e., physically moving or shipping the pre-packaged backing element to a second site.

Once the compression device with the array pre-assembled or pre-packaged therein is received by a user at the second site, a sample is contacted to the array and the substrate having an array thereon is contacted with a backing element, where the order thereof may be reversed or otherwise altered as convenient for a given procedure. Next, the compression device is closed and a compression force is applied to the backing element supported sample/assay structure, as described above, and an array assay, e.g., a hybridization assay, is performed using the compression device and pre-packaged array. Following completion of the array assay, the compression force is relieved and the substrate having at least one array is removed from the compression device, positioned on an array scanner or reader and the at least one array is scanned by the array reader to obtain a result, as described above. As mentioned above, the substrate may be positioned in a substrate receiving frame and/or array holder prior to placement in a compression device and the substrate may be retained in the substrate receiving frame and/or array holder during the scanning or reading of the at least one array, i.e., the substrate receiving frame and/or array holder may be operatively mounted on a scanner so that the array(s) may be scanned or read while retained in the substrate receiving frame and/or array holder to obtain a result.

In certain embodiments, the foregoing general assay methods do not include those assay methods described in U.S. application Ser. No. 09/919073, filed on Jul. 30, 2001.

The subject methods may include a step of transmitting data from at least one of the detecting and deriving steps, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

Kits

Finally, kits for use in practicing the subject methods are also provided. The subject kits at least include the subject compression devices, as described above, which devices may include one or more backing elements having one or more container elements. The subject kits may also include one or more arrays. The kits may further include one or more additional components necessary for carrying out an analyte detection assay, such as sample preparation reagents, buffers, labels, and the like. As such, the kits may include one or more containers such as vials or bottles, with each container containing a separate component for the assay, and reagents for carrying out an array assay such as a nucleic acid hybridization assay or the like. The kits may also include a denaturation reagent for denaturing the analyte, buffers such as hybridization buffers, wash mediums, enzyme substrates, reagents for generating a labeled target sample such as a labeled target nucleic acid sample, negative and positive controls.

In addition to the above components, the subject kits also typically include written instructions for practicing the subject methods. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above discussion that the above described invention provides devices and methods for performing array assays which are simple to use, have minimal components, and can be used with a multitude of different array formats. The above described invention provides for a number of advantages, including fluid loss prevention and the ability to test multiple samples with multiple arrays without cross-contamination. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of assaying a sample for the presence of at least one analyte, said method comprising:
   (a) contacting said sample with a first surface of a first substrate to produce a substrate supported sample;
   (b) placing said substrate supported sample in contact with a second substrate to form a structure comprising said first and second substrates spaced-apart from each other by a separator, wherein one of said substrates is an array substrate having at least one array of at least two distinct biopolymers attached to different and known locations on a surface of said array substrate;
   (c) applying a compression force to compress said structure together using a slideably engageable compression device comprising a base and a cover configured to apply a compression force to said structure when present in said compression device; and
   (d) reading said at least one array to obtain a result.

2. The method according to claim 1, wherein said separator is a fluid barrier.

3. The method according to claim 1, wherein said fluid barrier provide one or more container elements.

4. The method according to claim 1, wherein said compression device applies opposing forces to said first and second substrates.

5. The method according to claim 1, wherein said compression force is applied uniformly.

6. The method according to claim 1, wherein said array is a nucleic acid array.

7. The method according to claim 1, wherein said analyte is a nucleic acid.

8. The method according to claim 1, wherein said array is a polypeptide array.

9. The method according to claim 1, wherein said analyte is a polypeptide.

10. The method according to claim 1, wherein said method further comprises a data transmission step in which said result is transmitted from a first location to a second location.

11. The method according to claim 10, wherein said second location is a remote location.

* * * * *